(12) United States Patent
O'Neil et al.

(10) Patent No.: US 6,171,342 B1
(45) Date of Patent: Jan. 9, 2001

(54) MEDICAL FASTENING SYSTEM

(75) Inventors: Michael J. O'Neil, West Barnstable; Arnold Oyola, Taunton; Dennis Sullivan, Sandwich; Amit Birla, Mansfield; John E. Slamin, Wrentham; Dennis P. Colleran, Plainville; Stefan M. Gabriel, Lakeville; George B. Cipolletti, Duxbury, all of MA (US); Richard E. Jones, Dallas, TX (US)

(73) Assignee: Depuy Orthopaedics, Inc., Warsaw, IN (US)

(*) Notice: Under 35 U.S.C. 154(b), the term of this patent shall be extended for 0 days.

(21) Appl. No.: 09/050,509

(22) Filed: Mar. 30, 1998

Related U.S. Application Data

(63) Continuation-in-part of application No. 08/696,495, filed on Aug. 14, 1996, now Pat. No. 5,824,097, which is a continuation-in-part of application No. 08/685,289, filed on Jul. 23, 1996, now Pat. No. 5,182,921.

(51) Int. Cl.$^7$ ...................................................... A61F 2/38
(52) U.S. Cl. ................................... 623/20.15; 623/20.34; 623/20.32
(58) Field of Search ............................ 623/20.14, 20.15, 623/20.16, 20.32, 20.34, 20.35, 20.36

(56) References Cited

U.S. PATENT DOCUMENTS

| | | | |
|---|---|---|---|
| 4,219,893 | 9/1980 | Noiles | 3/1.911 |
| 4,301,553 | 11/1981 | Noiles | 3/1.911 |
| 4,404,691 | 9/1983 | Buning et al. | 3/1.911 |
| 4,578,081 | 3/1986 | Harder et al. | 623/22 |
| 4,624,673 | 11/1986 | Meyer | 623/16 |
| 4,714,471 | 12/1987 | Grundei | 623/20 |
| 4,790,852 | 12/1988 | Noiles | 623/18 |
| 4,790,854 | 12/1988 | Harder et al. | 623/20 |
| 4,822,366 | 4/1989 | Bolesky | 623/20 |
| 4,834,758 | 5/1989 | Lane et al. | 623/20 |
| 4,846,839 | 7/1989 | Noiles | 623/18 |
| 4,888,021 | 12/1989 | Forte et al. | 623/20 |
| 4,904,110 | 2/1990 | Klein | 403/379 |
| 4,936,853 | 6/1990 | Fabian et al. | 623/20 |
| 4,944,757 | 7/1990 | Martinez et al. | 623/20 |
| 4,985,037 | 1/1991 | Petersen | 623/20 |
| 5,011,496 | 4/1991 | Forte et al. | 623/20 |
| 5,019,103 | 5/1991 | Van Zile et al. | 623/20 |
| 5,057,111 | 10/1991 | Park | 606/69 |
| 5,127,914 | 7/1992 | Calderale et al. | 606/65 |
| 5,133,760 | 7/1992 | Petersen et al. | 623/20 |
| 5,137,535 | 8/1992 | Keller | 623/20 |
| 5,152,796 | 10/1992 | Slamin | 623/20 |
| 5,194,066 | 3/1993 | Van Zile | 623/20 |
| 5,269,784 | 12/1993 | Mast | 606/69 |
| 5,290,313 | 3/1994 | Heldreth | 623/20 |
| 5,326,359 | 7/1994 | Oudard | 623/20 |
| 5,330,534 | 7/1994 | Herrington et al. | 623/20 |
| 5,336,225 | 8/1994 | Zang | 606/73 |
| 5,370,701 | 12/1994 | Finn | 623/20 |
| 5,397,360 | * 3/1995 | Cohen et al. | 623/20 |
| 5,405,395 | 4/1995 | Coates | 623/20 |
| 5,413,605 | 5/1995 | Ashby et al. | 623/20 |
| 5,556,433 | * 9/1996 | Gabriel et al. | 623/20 |
| 5,609,641 | 3/1997 | Johnson et al. | 623/20 |
| 5,683,469 | 11/1997 | Johnson et al. | 623/20 |
| 5,782,921 | * 7/1998 | Colleran et al. | 623/20 |

FOREIGN PATENT DOCUMENTS

| | | | |
|---|---|---|---|
| 0473375 | 3/1992 | (DE) | 411/398 |
| 0307655 | 8/1988 | (EP) | A61F/2/38 |
| 0529408 | 3/1993 | (EP) . | |
| 0531263 | 3/1993 | (EP) | A61F/2/38 |
| 1575278 | 5/1978 | (GB) | A61F/1/03 |
| 2259253 | 8/1992 | (GB) | A61F/2/02 |

OTHER PUBLICATIONS

Johnson & Johnson Orthopaedics Research & Development "P.F.C.® Modular Knee System Research Data and Laboratory Testing," cover and pp. 8, 36 and 37 (1989).

* cited by examiner

Primary Examiner—David J. Isabella
(74) Attorney, Agent, or Firm—Nutter, McClennen & Fish, LLP

(57) ABSTRACT

A medical fastening system for a modular knee prosthesis system includes a femoral component having a first surface, a second surface, and an aperture extending therebetween. A modular adapter element has a first end that is mountable adjacent the first surface of the femoral component and a second, mating end that is engagable with a second prosthesis component. The system also includes a first bolt that mates the adapter element to the femoral component. Various connection options are possible to secure different components of the system to each other.

49 Claims, 15 Drawing Sheets

MEDICAL FASTENING SYSTEM

CROSS-REFERENCE TO RELATED APPLICATIONS

The present application is a continuation-in-part of commonly assigned U.S. patent application Ser. No. 08/696,495, filed Aug. 14, 1996, entitled "Medical Fastening System," now U.S Pat. No. 5,824,097 which is a continuation in-part of commonly assigned Pat. application No. 08/685,289, filed Jul. 23, 1996, entitled "Modular Knee Prosthesis" now U.S. Pat. No. 5,782,921.

FIELD OF THE INVENTION

This invention relates to joint prostheses, and more particularly to modular knee joint prostheses employed during knee arthroplasty procedures.

BACKGROUND OF THE INVENTION

Knee arthroplasty is a well-known surgical procedure by which a diseased and/or damaged natural knee joint is replaced by a prosthetic knee joint. Typical knee prostheses include a tibial component, a femoral component, and a patellar component. The femoral component generally includes a pair of spaced apart condylar portions, the superior surfaces of which articulate with a portion of the tibial component. A femoral stem assembly, used to provide lateral stability to the replaced knee joint, seats within the medullary canal of a distal portion of a femur, and is typically coupled to the femoral component by specialized coupling devices, such as a collar and bolt. Some prosthetic knee joints include a structure known as a Morse taper post that extends from the inferior surface of the femoral component to mate with a femoral sleeve that is securable to the femoral stem assembly.

The femoral sleeve, which helps to fill spaces at the opening of the medullary canal, can also provide for a modular assembly allowing a surgeon to select the most appropriate femoral stem from a selection of stems having different lengths and diameters for attachment to one of a selection of femoral components. This modular configuration significantly reduces the number of individual components that must be purchased, stocked, and used during a surgical procedure. Although the femoral stem, whatever its dimensions, is usually angled laterally with respect to the inferior surface of the femoral component and either off-set anteriorially/posterially or at a central location, it is sometimes desirable to orient the femoral stem perpendicularly with respect to the inferior surface. For example, depending on particular patient requirements, the femoral stem may need to be offset fore or aft with respect to the front of the femoral component. Similarly, the femoral stem may need to be angled varying degrees to the left or right with respect to the front of the femoral component. The Morse taper post, however, is integrally cast as a unitary and indivisible portion of the femoral component. Furthermore, there is a requirement for a range of sizes of the overall femoral component. Therefore, in order to accommodate all of the possible combinations of overall femoral component size, fore/neutral/aft positioning of the Morse taper post, and left/perpendicular/right angling of the Morse taper post, a doctor or hospital is required to maintain an undesirably substantial stock of knee prosthesis components.

Despite the existence of knee joint prostheses having modular components, there remains a need for a modular knee joint prosthesis that has greater versatility to accommodate differing patient anatomy and joint conditions. It is thus an object of the invention to provide a modular knee prosthesis having greater versatility to accommodate different patient anatomy and joint conditions while maintaining a relatively low component count. It is another object of the invention to provide a modular knee prosthesis having components that are physiologically and geometrically compatible with different anatomical conditions. Still another object of the invention is to provide a modular knee prosthesis that is suitable for use in both right and left knee procedures. Other general and more specific objects of the invention will in part be apparent from the drawings and description that follow.

SUMMARY OF THE INVENTION

The present invention relates to a versatile modular knee joint prosthesis system that offers numerous options for femoral component fixation and stability while reducing the overall component count. Components of the modular prosthesis of the invention are able to be used with both right and left side prostheses to provide angled, non-angled, offset and non-offset orientation of femoral stem components. Moreover, the system of the invention provides various options for attaching prosthesis components, such as metaphyseal augments and femoral stems, to the femoral prosthesis component.

In an exemplary embodiment of the invention, a modular knee prosthesis includes a femoral component, a bolt, and a Morse taper post. The femoral component has a superior surface, an inferior surface, and an aperture extending therebetween. The bolt includes a head portion engagable with the superior surface of the femoral component to inhibit movement of the bolt through the femoral component, and an elongate shaft portion that extends from the head portion of the bolt. The elongate shaft portion has a length sufficient to protrude through the aperture beyond the inferior surface of the femoral component. The Morse taper post is engagable with the elongate shaft portion of the bolt to retain the Morse taper post in a fixed position with respect to the femoral component and the distal end of the Morse taper post is introducible within a femoral sleeve.

The modular knee prosthesis can further include a collar interposable between the Morse taper post and the inferior surface of the femoral component. The collar can position the elongate shaft portion of the bolt or the Morse taper post orthogonally or at an angle, in the medial or lateral directions, with respect to the inferior surface of the femoral component.

Additionally, the aperture of the femoral component can be configured to allow the shaft portion of the bolt to be extended through the aperture at a predetermined angle with respect to the inferior surface of the femoral component and be held at the predetermined angle by a collar. The aperture and the bolt are cooperatively configured to position the Morse taper post fore and aft with respect to a central reference location.

In another embodiment of the invention, a modular knee fastening system for a modular knee prosthesis includes a washer engagable with a bolt and a femoral component so that a portion of the bolt shaft protrudes through an aperture in the washer and an aperture in the femoral component. The washer can include an aperture that is in the center of the washer, off-center, or lobed to permit selective placement of the bolt with respect to the femoral component.

In yet another embodiment of the invention, a medical fastening system for a modular knee prosthesis includes a femoral component having an aperture. A washer having an aperture alignable with at least a portion of the aperture in the femoral component engages the femoral component to inhibit movement of the washer through the aperture in the femoral component. A bolt engages the washer and an elongate shaft portion of the bolt protrudes from the femoral component through the aperture in the washer and the aperture in the femoral component to engage a Morse taper post or femoral stem. The configuration of the washer aperture, its location in the washer, and the orientation of the washer within the femoral component determine the fore and aft positioning of the Morse taper post or femoral stem. The Morse taper post or femoral stem can be provided with a canted base to angle the post or stem with respect to the femoral component.

In a further embodiment, the knee prosthesis system of the invention includes a first prosthesis component (e.g., a femoral component of a knee joint prosthesis), which has a first surface, a second surface, and an aperture extending between the two surfaces. A modular adapter element has a first end that is mountable adjacent the first surface of the first prosthesis component and a second, mating end that is engagable with a second prosthesis component. The first end of the modular adapter element includes a bore that extends therein. The system also includes a first bolt having a head portion engagable with the second surface of the prosthesis component to prevent the bolt from passing through the first prosthesis component. An elongate shaft, which has a length sufficient to protrude through the aperture and into the bore of the modular adapter, extends for the bolt head. Ideally, the bolt is effective to secure the first end of the modular adapter to the first surface of the first prosthesis component.

Various connection options are possible to secure the various components of the system to each other. For example, the first bolt and the adapter element may be secured to one another by a threaded engagement, or by a tapered fit. The adapter element may be secured to the second prosthesis component by a variety of connection options as well.

Further, the bore in the adapter element may be centered with respect to a longitudinal axis of the adapter, or it may be offset either anteriorly or posteriorly. The mounting surface of the adapter element, which abuts the first prosthesis component, may be parallel to a transverse axis of the adapter element, or it may be angled, such as in the medial-lateral plane, with respect to the transverse axis.

The second prosthesis component may be a femoral stem, or it may be a metaphyseal augment. In embodiments in which the second prosthesis component is a metaphyseal augment, this augment may attach to a femoral stem.

BRIEF DESCRIPTION OF THE DRAWINGS

The foregoing and other objects, features and advantages of the invention will be apparent from the following description and the accompanying drawings, in which like reference characters refer to the same parts throughout the different views.

DETAILED DESCRIPTION OF THE INVENTION

Figure 1:
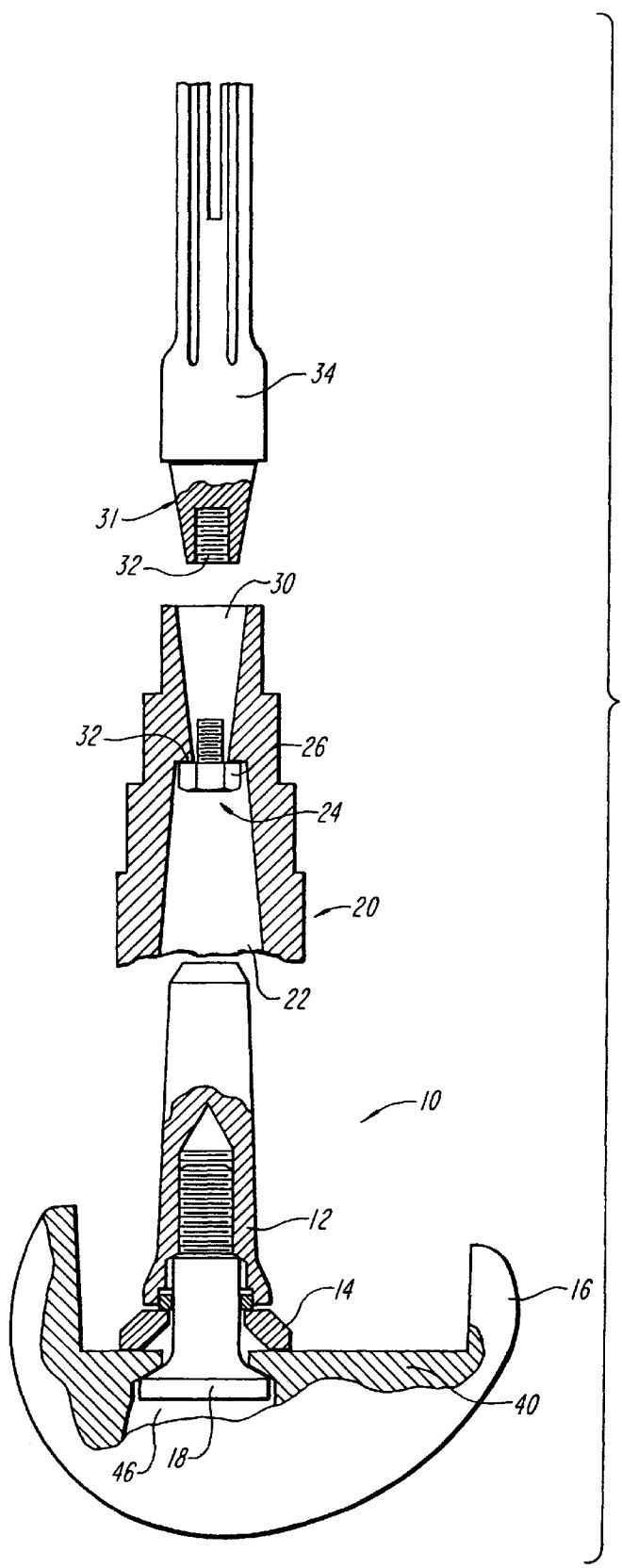
FIG. 1 is a cutaway exploded view of a modular knee prosthesis according to the present invention that includes a right knee femoral component.

As illustrated in FIG. 1, a modular knee prosthesis 10 of the invention includes a Morse taper post 12, a collar 14, a femoral component 16, and a securing bolt 18. Although the illustrated modular knee prosthesis 10 includes a femoral component 16 adapted for a right knee, the Morse taper post 12, collar 14, and securing bolt 18 are suitable for use, without modification, in association with a femoral component adapted for a left knee.

A femoral sleeve 20, adapted for mating with the Morse taper post 12, includes a first end that defines a first cavity 22 for receiving the distal end portion of the Morse taper post. In the illustration, the first cavity 22 is tapered to provide a friction fit over the Morse taper post 12. A femoral sleeve stem bolt 24, having a head 26 and a shank 28 is positionable within the femoral sleeve 20. The shank 28 projects into a second cavity 30 defined in the second end of the femoral sleeve 20. In an exemplary embodiment, the femoral sleeve 20 includes a constriction or shoulder 32 that prevents the head 26 from entering into the second cavity 30 or otherwise anchors the femoral sleeve stem bolt 24 within the femoral sleeve 20. The femoral sleeve stem bolt 24 is adapted to engage a mating portion 32 of a femoral stem 34 selected from a group of femoral stems having different lengths and diameters. The illustrated femoral stem has a tapered end 31 that is receivable within the second cavity 30 of the femoral sleeve, which has a complimentary taper. In other embodiments of the invention, the Morse taper post is directly matable with a femoral stem or other component without a femoral sleeve.

Figure 2:
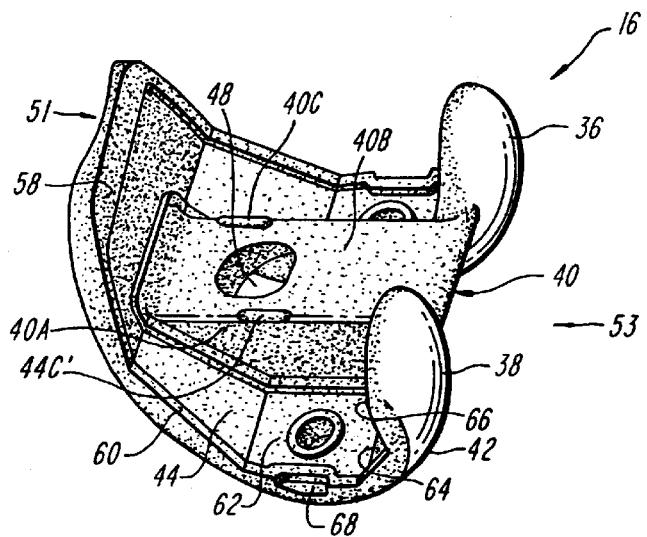
FIG. 2 is a perspective view of the femoral component of the modular knee prosthesis of FIG. 1.
Figure 3:
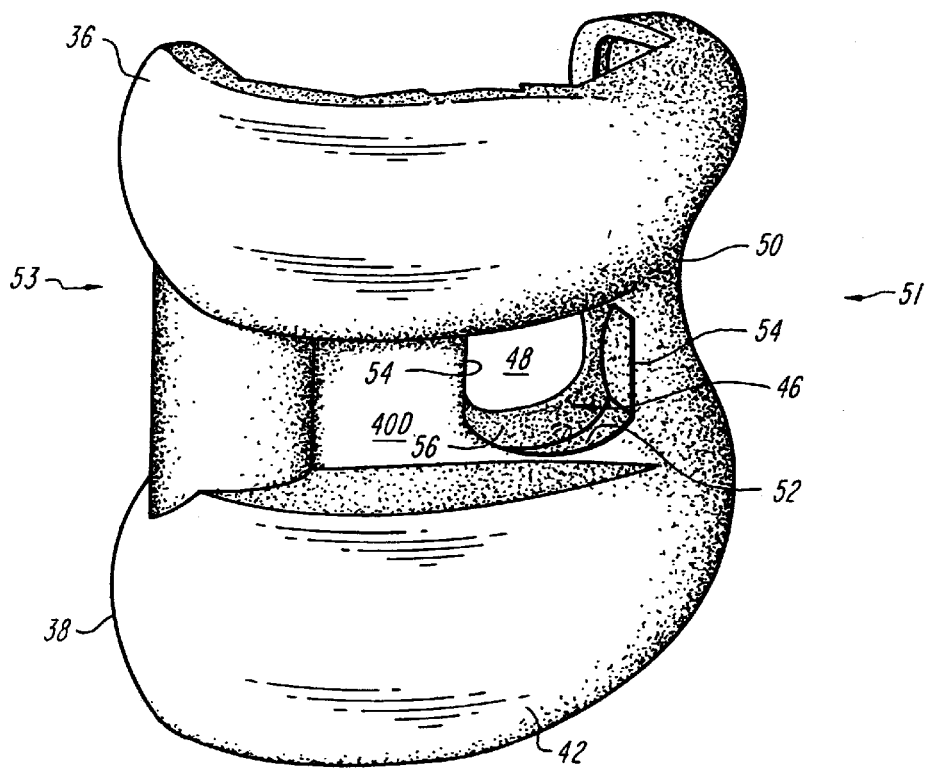
FIG. 3 is a bottom perspective view of the femoral component of FIG. 2.

Referring to FIGS. 1 through 3, the femoral component 16 has a pair of condylar portions 36, 38 that are connected by an intercondylar region or boss 40. The femoral component 16 has a superior articulation surface 42 and an opposed inferior surface 44. Further, the femoral component 16 has a posterior side 53 and an anterior side 51. The anterior side 51 of the femoral component 16 includes a patellar groove 50, shown in FIG. 3, within which seats a patellar prosthetic component (not shown). The superior surfaces 42 of the curved condylar portions 36, 38 articulate with a prosthetic tibial component (not shown) mounted on the head of the tibia, in a manner well known to those of ordinary skill in the art.

The boss structure 40 has a pair of substantially vertical side walls 40A that are generally orthogonal to a top, inferior surface 40B. The top surface 40B preferably has formed thereon a pair of raised ridges 40C that constitute a collar anti-rotation element, as described in further detail below.

With reference to FIGS. 1 and 3, the boss 40 has a cavity 46 formed within a bottom superior surface 40D. An aperture 48 defined by the cavity 46 extends between the superior and inferior surfaces 42, 44, respectively, of the boss structure 40 and has a selected shape such that it can be elongated either in the anterior-posterior direction or the medial-lateral direction. The shape of the aperture can be elliptical, oval, spherical, or of any other suitable shape that allows a sufficient amount of translation of the securing bolt shaft when the bolt is mounted within the aperture.

In the illustrated embodiment, the cavity 46 has a pair of arcuate medial and lateral side walls 52, and a pair of substantially flat anterior and posterior side walls 54 that form a bolt anti-rotation mechanism, as described in further detail below. The cavity 46 further includes an end wall 56 that has a substantially spherical or rounded shape for seating a correspondingly shaped head of the securing bolt 18.

The inferior surface 44 of the condylar portions 36, 38 forms a series of integral surfaces that extend between the anterior and posterior sides of the femoral component. Referring to FIG. 2, the inferior surface of each condylar portion comprises a substantially vertical anterior surface 58, an anterior chamfer surface 60, a substantially horizontal surface 62, a posterior surface 64, and a substantially vertical posterior surface 66. The surface 62 of each condylar portion has an indentation 68 that extends partly into the inferior surface of each condylar portion. The indentation allows the surgeon to grasp and handle the femoral component via a suitable handling instrument. Those of ordinary skill in the art will recognize that the femoral component 16, boss 40, and condylar portions 36, 38 can have a variety of shapes.

Figure 4A:
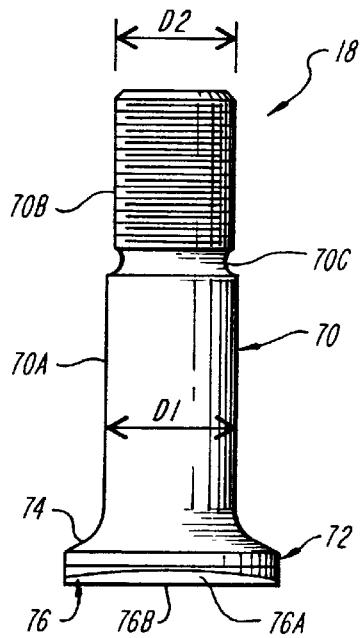
FIG. 4A is a side view of one embodiment of a securing bolt useful with the modular knee prosthesis of FIG. 1.

FIGS. 4A–5B illustrate preferred embodiments of the securing bolt 18 of FIG. 1. With reference to FIG. 4A, the bolt 18 of a first embodiment has a shaft portion 70 that extends upwardly and outwardly from a bolt head 72. The shaft has a lower unthreaded portion 70A that has an outer diameter (D1) less than the outer diameter of bolt head 72, and an upper, threaded portion 70B that is integral with the lower unthreaded portion 70A. An indented neck portion 70C may separate the upper and lower portions 70B, 70A of bolt 18. The outer diameter (D2) of the upper portion 70B can be slightly less than the outer diameter (D1) of the lower shaft portion 70A.

The bolt head portion 72 has a boss aperture-engaging surface 74, and an opposed, top surface 76 that includes a pair of canted surfaces 76A that join at an apex 76B. The aperture-engaging surface 74 can have a rounded or spherical shape complementary to that of the end wall 56 of the boss cavity 46. The mating engagement of the aperture-engaging surface 74 of the bolt head 72 and the shaped end wall 56 of the boss cavity 46 positions the bolt shaft within the aperture 48. The bolt shaft 70 extends from the boss top surface 40B at a selected angle determined by the shape of the aperture 48 and by the mounting angle of the collar 14. The shape of the aperture 48 helps determine the allowable angle and translational range of the bolt shaft by allowing the bolt shaft to angulate and translate within the confines of the aperture, and to eventually seat at a selected position therein, as described in further detail below. Although the end wall 56 and aperture-engaging surface 74 are shown with spherically-shaped contours, those of ordinary skill will recognize that other compatible configurations are possible.

Figure 4B:
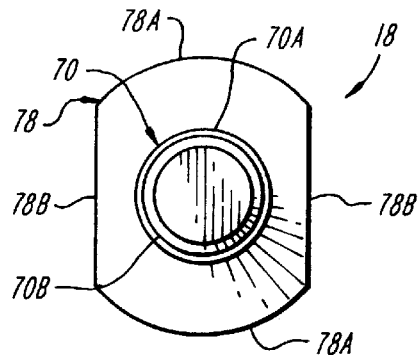
FIG. 4B is a top view of the securing bolt of FIG. 4A.

As illustrated in FIG. 4B, the top surface 76 of the bolt head 72 has a peripheral surface 78 that is defined by a pair of opposed, arcuate sides 78A and a pair of opposed, substantially flat sides 78B. The flat sides 78B matingly engage the flat side walls 54 of the boss cavity 46 and cooperate therewith to secure the bolt within the cavity and to prevent unwanted rotation of the bolt when secured therein.

With further reference to FIG. 4B, in one embodiment the bolt is constructed such that the shaft portion 70 of the bolt extends from a generally centrally located position on the bolt head 72. This arrangement allows the bolt shaft to extend from the inferior surface of the femoral component when the bolt is mounted within the boss aperture at a selected location and desired angle relative to the inferior surface 40B.

Figure 5A:
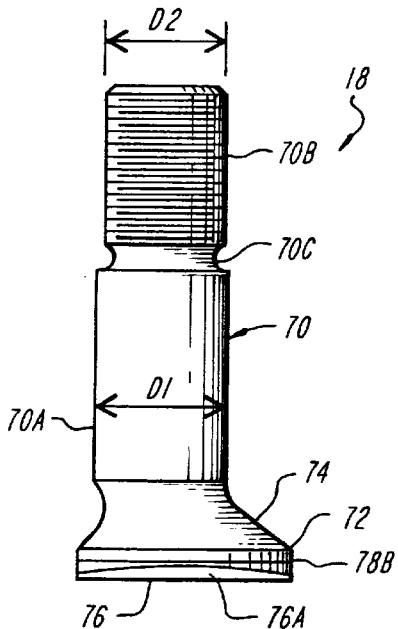
FIG. 5A is a side view of an alternate embodiment of a securing bolt useful with the modular knee prosthesis of FIG. 1.
Figure 5B:
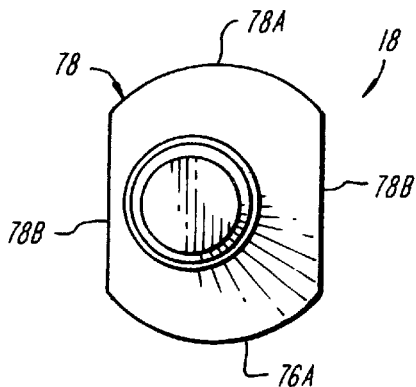
FIG. 5B is a top view, from the shaft, of the securing bolt of FIG. 5A.

FIGS. 5A and 5B illustrate another embodiment of a securing bolt 18 constructed according to the invention. In this embodiment, bolt 18 is similar to that described above and shown in FIGS. 4A and 4B, except that the shaft 70 is positioned on the bolt head 72 in an offset, non-centered position. As illustrated, the shaft portion 70 of the bolt extends upwardly from a position axially offset a selected distance from a generally centrally located position of the bolt head 72. In an exemplary embodiment, the shaft is offset from this generally centrally located position is in the range of about 0 mm to about 5 mm. Preferably, the offset distance is about 2 mm.

This offset construction of the bolt 18 allows the bolt shaft 70 to extend from the boss inferior surface 40B, when the bolt is mounted within the boss aperture, offset from a central or neutral position in either an anterior or a posterior direction, in addition to being oriented at a selected angle and axial orientation relative to the inferior surface 40B of the femoral component 16. For example, an offset bolt (FIGS. 5A and 5B) oriented in either an anterior or posterior direction may be necessary for differing anatomies, or where bony deficiencies exist in certain areas of the femur. By contrast, the illustrated bolt of FIGS. 4A and 4B can be used in both left or right side prostheses where no bolt offset is desired. Thus, the bolts illustrated in FIGS. 4A, 4B, 5A and 5B can be used in both right and left side prostheses where an anterior or posterior, or medial or lateral offset is needed.

Figure 6A:
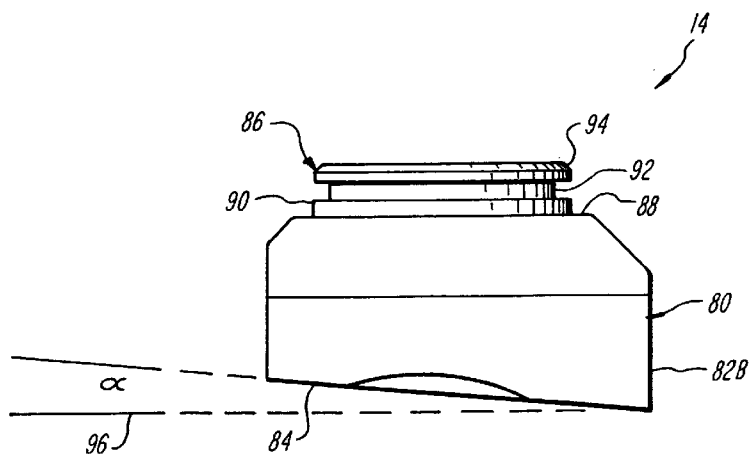
FIG. 6A is a side view of a collar useful with the modular knee prosthesis of FIG. 1.
Figure 6B:
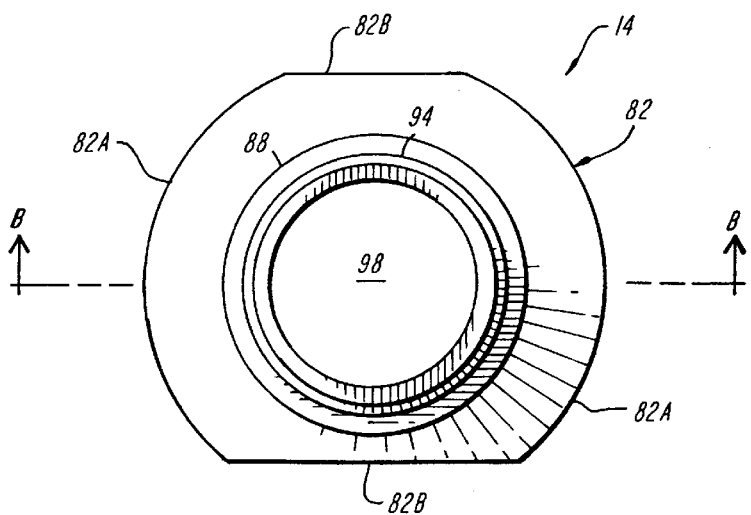
FIG. 6B is a top view of the collar of FIG. 6A.

With reference to FIGS. 6A and 6B, the collar 14 has a central body portion 80 that has an outer peripheral surface 82 and a boss engaging surface 84. The collar 14 can further include a neck portion 86 that extends upwardly from a seating surface 88 if required to mate with a particular Morse taper post configuration. The neck 86 can include a first annular portion 90 and a stepped annular portion 92. A lip 94 formed along the top of the stepped annular surface 92 overhangs the first annular portion 90. The proximal end of the Morse taper post 12, when assembled with the collar 14, engages the seating surface 88.

The boss engaging surface 84 can be canted to form an angle with a transverse plane 96. The transverse plane is defined as the horizontal plane that extends through the knee of an upright subject and that is orthogonal to both the coronal plane and the sagittal plane, as will be appreciated by those having ordinary skill in the art. The engaging surface 84 and the top, inferior surface 40B of the boss 40, which lies in the transverse plane, form a mounting angle " " when the collar is assembled with the femoral component and engages the boss top surface. The angle " " is preferably between about 0° and about 15°. According to one practice of the invention, the boss engaging surface 84 can be canted in the anterior-posterior direction to either the anterior or posterior side as measured in the sagittal plane. Likewise, the surface 84 can be canted in the medial-lateral direction to either the medial side or the posterior side as measured in the coronal plane. Preferably, the angle " " can range between about 0° and about 15° in any direction. This varied collar angulation provides a plurality of mounting angles for the Morse taper post 12 that is compatible with the various possible orientations of the femoral stem when mounted within the distal portion of the femur. Those of ordinary skill in the art will readily appreciate that the boss mounting surface 84 can be configured to provide any combination of coronal and sagittal plane angulations that are constrained by the foregoing angle ranges.

The collar 14 can be used with either right or left side knee prostheses. Generally, the collar is positioned such that the angle is to the lateral side of the prosthesis, as measured in the coronal plane. The same collar can be used in either a left or right side prosthesis by simply reversing the orientation of the collar on the prosthesis to ensure a lateral angle for the Morse taper post 12.

With reference to FIG. 6B, the collar peripheral surface 82 has a pair of opposed arcuate sides 82A and a pair of opposed, flat sides 82B. Flat sides 82B are adapted to engage the raised ridges 40C of the boss top surface 40B. The mating contact between the raised ridges 40C and the flat sides 82B of the collar peripheral surface prevents unwanted rotation of the collar when it is mounted on the boss top surface 40B.

Figure 6C:
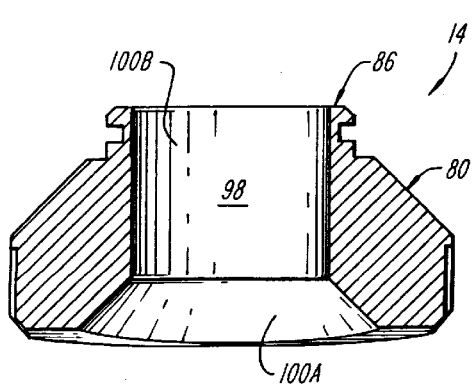
FIG. 6C is a cross-sectional view of the collar of FIG. 6A taken along line B—B of FIG. 6B.

As illustrated in FIG. 6C, the collar 14 further has a central aperture 98 that seats and orients the bolt shaft 70. The aperture 98 has a funnel-like portion 100A adjacent the boss mounting surface 84, and a cylindrical portion 100B that extends from the funnel-like portion 100A to the neck 86 of the collar. The funnel-like portion 100A provides an additional clearance space for bolt insertion.

An exemplary modular knee prosthesis can be assembled in the following manner. The collar 14 is mounted on the top surface 40B, e.g., inferior surface, of the boss 40, and the flat sides 82B of the collar are aligned with the raised ridges 40C. The securing bolt 18 is then inserted into the boss cavity 46 from the underside of the boss and through the boss aperture 48, such that the bolt shaft extends upwardly from the boss inferior surface 40B. The spherical engaging surface 74 of the bolt head 72 mates with and engages the similarly configured end wall 56 of the cavity. The selected shape of the cavity end wall allows the bolt shaft to seat within the cavity at an angle that is determined by the collar 14. The boss mounting surface 84 of the collar 14 determines the angle at which the bolt shaft protrudes into and extends from the collar 14. The threaded portion 70B of the bolt shaft 70 threadedly a threaded portion of the Morse taper post to bind the Morse taper post and collar to the femoral component. In this axially successive assemblage, the collar is pressure fitted between the Morse taper post and boss by the threaded engagement of the bolt and stem.

A significant feature of the present invention is the complementary shape of the cavity end wall and the mounting surface of the securing bolt head, which cooperate to position the securing bolt at a selected angle determined by the collar mounting angle. The varied positions in which the securing bolt shaft can be oriented are facilitated by the selected shape of the aperture. In the modular knee prosthesis of the present invention, the shaft of the securing bolt can be centrally located or offset, depending upon the surgeon's judgment. Additionally, since the collar is pressure fitted between the Morse taper post and boss, the Morse taper post and collar can be separately provided in a packaged modular knee prosthesis. For example, the packaged modular knee prosthesis can include a femoral component, an offset and/or a non offset type securing bolt, a collar or collars having a 5 degree and/or a 7 degree canted mounting surface, and a Morse taper post. The packaged modular knee prosthesis 10 of the invention can further include a femoral sleeve and one or more femoral stems.

Although the securing bolt, collar, and Morse taper post have been illustrated in co-axial configurations, such configurations are not required by the invention. For example, depending on the dimensions of the securing bolt, collar and Morse taper post, the securing bolt can project through the aperture in the femoral component and the collar so as to be perpendicular to the inferior surface; however, the boss mounting surface or the neck of the collar can be canted to angle the Morse taper post as desired.

Figure 7:
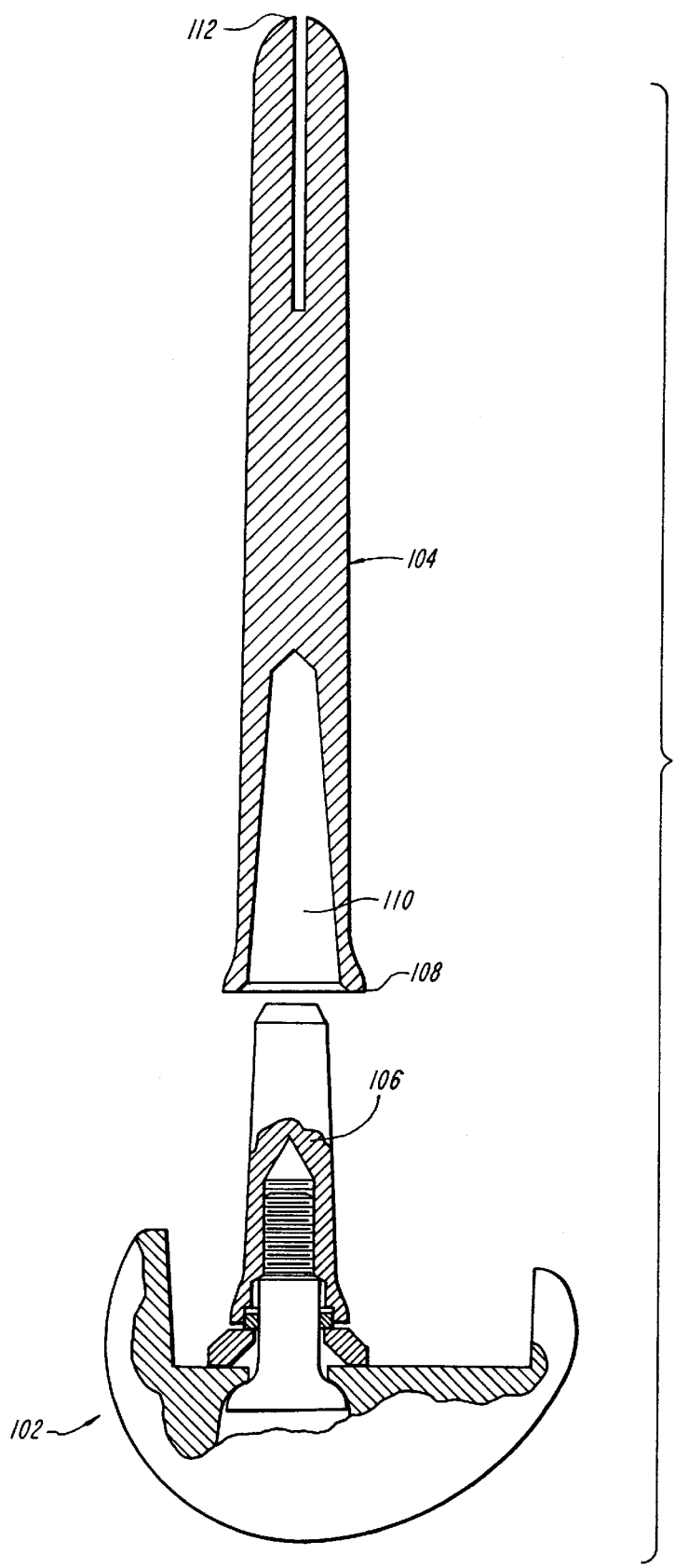
FIG. 7 is a cutaway exploded view of an a modular knee prosthesis according to the present invention, wherein a femoral stem is directly mountable on a Morse taper post.

Referring now to FIG. 7, a modular knee prosthesis 102 is illustrated that does not include a femoral sleeve. In this embodiment, a femoral stem 104 is adapted for mating directly with a Morse taper post 106. More particularly, the femoral stem includes a first end 108 that defines a cavity 110 that is tapered to provide a friction fit over the Morse taper post 106. A second end 112 of the femoral stem is adapted for placement in a patient's medullary canal. In substantially all other respects, however, the remaining components of the modular knee prosthesis are identical to the components illustrated in FIG. 1.

With respect to each of the preceding embodiments, a modular collar 14 increases the adaptability of the modular knee prosthesis 10. However, other embodiments of the invention include a Morse taper post that has features of the collar, such as a canted boss mounting surface, funnel-like portion, opposed arcuate sides, and opposed flat sides. As these configurations could preclude the Morse taper post from rotating during assembly, because its base is lodged between the raised ridges of the femoral component, a securing bolt can be provided that is rotatable with respect to the femoral component to urge the securing bolt and Morse taper post together.

Figure 8:
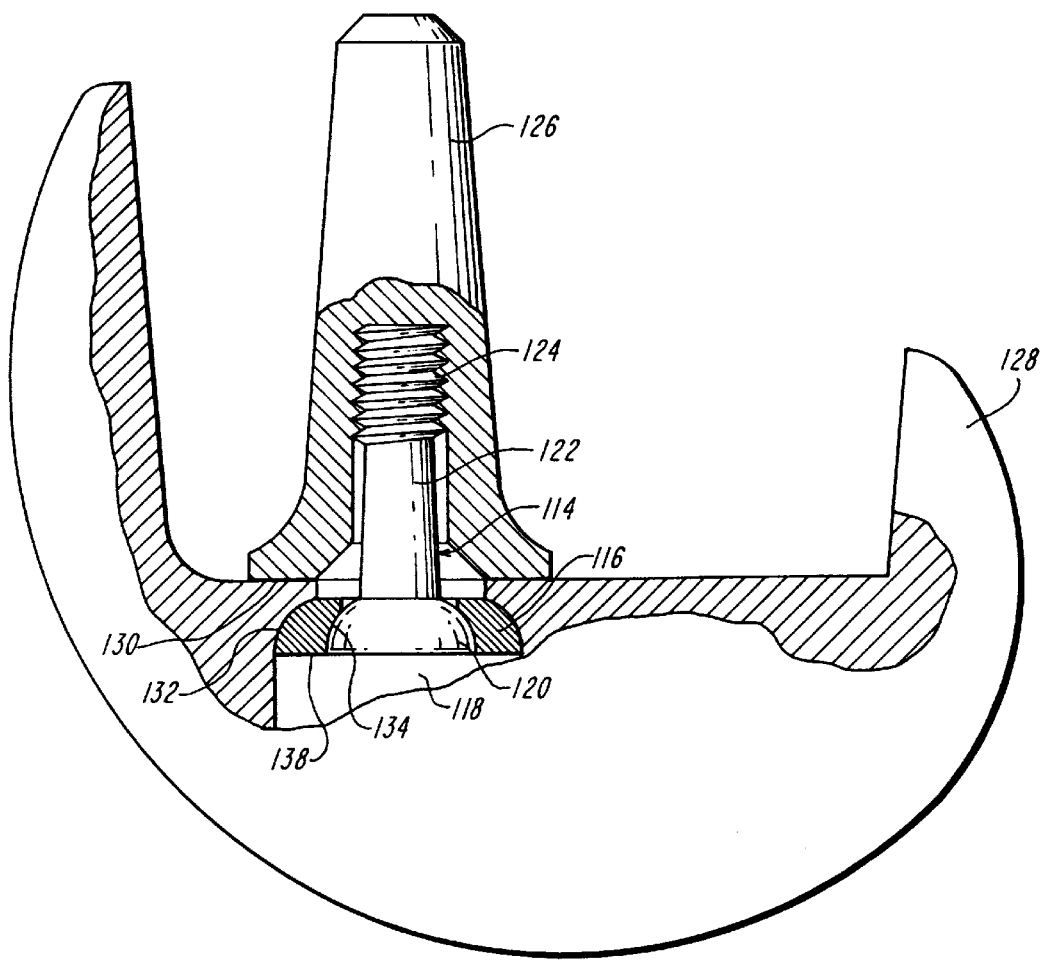
FIG. 8 is a cutaway view of an alternative embodiment of the invention having a bolt and washer fastening system and that does not include a collar.
Figure 9:
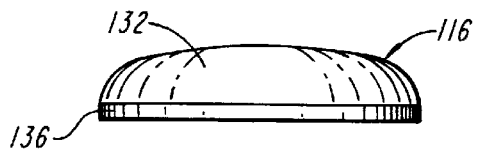
FIG. 9 is a side view of a washer in accordance with the invention.

For example, FIG. 8 is a cutaway view of an alternative embodiment of the invention having a securing bolt and washer fastening system that does not include a collar, for use with a femoral component. In this embodiment, the securing bolt of FIGS. 1–6 is replaced by a bolt 114 and a washer 116, wherein the bolt and washer are rotatable with respect to each other and are collectively cooperative with the configuration of a boss cavity 118 to facilitate angulation and translation of the bolt as described above with respect to FIGS. 1–7. The bolt includes a head 120, a shank 122, and an engagement feature 124 such as threads. A supplemental component 126, such as a Morse taper post or femoral stem includes features, such as threads, that cooperate with the engagement feature 124 of the bolt 114 to allow the bolt to be firmly mated to the supplemental component and a femoral component 128. As a Morse taper post is illustrated in FIG. 8, the supplemental component 126 will be referred to as such during the descriptions that follow.

The lateral angulation of the Morse taper post 126 with respect to the femoral component 128 is determined by the cant of a boss mounting surface 130. In FIG. 8, the plane defined by the boss mounting surface 130 is substantially perpendicular to the longitudinal axis of the Morse taper post to provide a neutral or 0 degree orientation. In other embodiments, the boss mounting surface defines a plane that is not perpendicular to the longitudinal axis of the Morse taper post to provide a selected angulation to the right or left with respect to the front of the femoral component.

Positioning or translation of the bolt 114 fore and aft is accomplished by selection of an appropriate washer 116 as illustrated in FIGS. 9–16. Each of the illustrated washers 116 includes a spherical boss-engaging or inferior surface 132, a contoured bolt head-engaging or superior surface 134, a peripheral surface 136, a top surface 138, a pair of opposed, arcuate sides 140, and a pair of opposed substantially flat sides 142. The flat sides 142 matingly engage a flat side wall of the boss cavity 118 and cooperate therewith to secure the washer 116 within the cavity and prevent unwanted rotation of the washer in a manner similar to that described above with respect to FIG. 4B.

Figure 10:
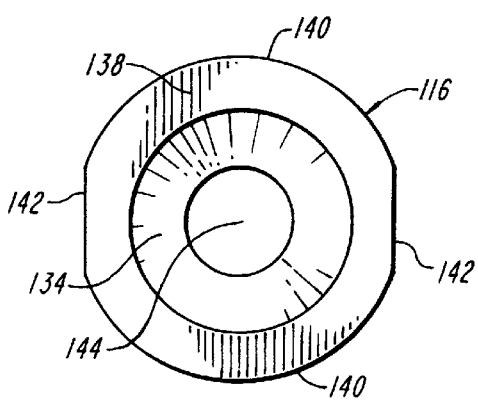
FIG. 10 is a top view of a washer in accordance with the invention.
Figure 11:
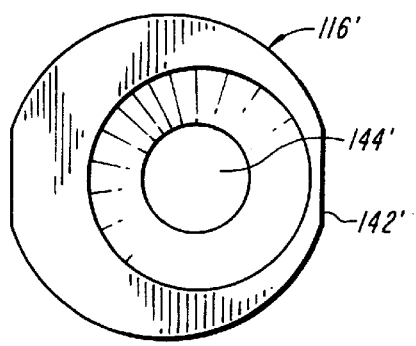
FIG. 11 is a top view of an alternative embodiment of a washer in accordance with the invention.

Referring now to FIG. 10, a top view of a washer 116 in accordance with the invention is illustrated, wherein an aperture 144 is in the center of the washer. A washer having this configuration is selected when no offset of the bolt 114 is required. By contrast, FIG. 11 illustrates a washer 116' wherein an aperture 144' is not at center of the washer, but is offset toward one of the substantially flat sides 142'. Thus, offset of the bolt 114 can be achieved with this washer by orienting the washer within the boss cavity 118 so that the aperture 144' is either closer to the front or the back of the femoral component 128.

Figure 12:
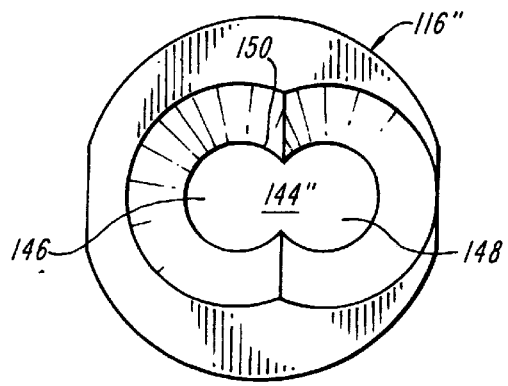
FIG. 12 is a top view of an yet another embodiment of a washer in accordance with the invention.
Figure 13:
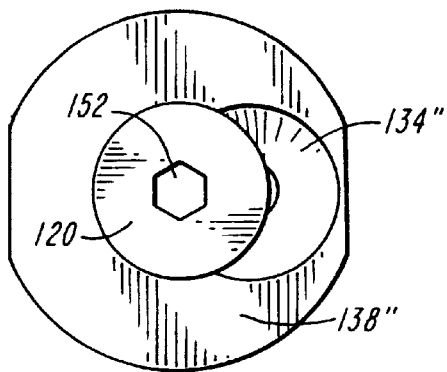
FIG. 13 is an end view of the washer of FIG. 12 in association with a bolt in a first position.
Figure 15:
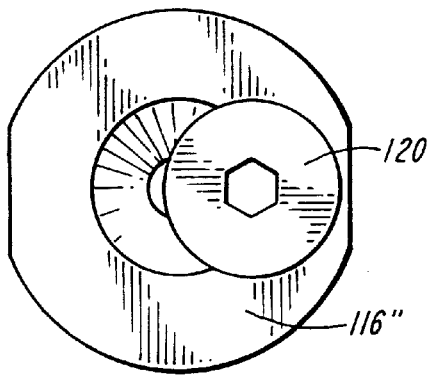
FIG. 15 is an end view of the washer of FIG. 12 in association with a bolt in a second position.

FIG. 12 illustrates an embodiment of the washer 116" having a double-lobed aperture 144", wherein each of the aperture lobes 146 and 148 is dimensioned to receive the bolt shank 122 therethrough. A neck portion 150 locally reduces the diameter of the aperture 144" and defines the first and second lobes 146, 148. At the neck portion 150, the aperture 144" has a smaller diameter than the bolt shank 122. However, the open configuration of the neck portion 150 allows a curved side portion of the bolt head or shank to extend into the principally unoccupied lobe as shown in FIGS. 13 and 15. This double-lobed configuration provides particular benefits in an application requiring a bolt to be positioned in either of a first or a second precisely defined location, but wherein the required bolt shank or head dimensions in association with the close proximity of the first location to the second location preclude the provision of two separate and distinct apertures. Additionally, a double-lobed configuration having a first lobe centrally located and an offset second lobe allows a single washer to be used in a kit to provide fore, neutral, and aft positioning of the bolt 120 by appropriate orientation of the washer within the femoral component and insertion of the bolt through on of the lobes.

Figure 14:
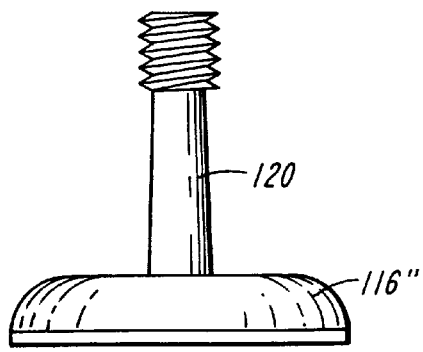
FIG. 14 is a side view of the bolt and washer of FIG. 13.
Figure 16:
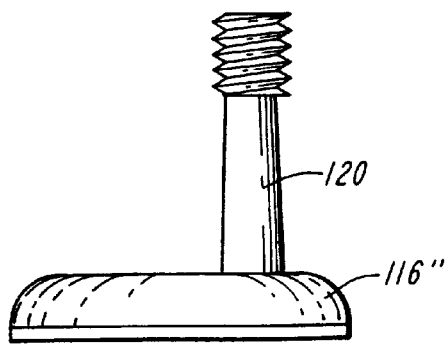
FIG. 16 is a side view of the bolt and washer of FIG. 15.

FIG. 13 is an end view of the washer 116" of FIG. 12 in association with a bolt in a first, central position and FIG. 14 is a side view of the bolt and washer of FIG. 13. The bolt 120 is illustrated with a slot 152 having six flattened sides suitable for engaging a hex wrench; however, the bolt head can be provided with other configurations known to those skilled in the art to permit the bolt to be tightened with a tool or by hand. FIG. 15 is an end view of the washer of FIG. 12 in association with a bolt in a second, offset position and FIG. 16 is a side view of the bolt and washer of FIG. 14.

Thus, an exemplary kit may include a selection of washers, a single bolt, and a selection of Morse taper posts and/or femoral stems, and be assembled in the following manner. A Morse taper post having the desired angulation is selected and mounted on the top surface of the boss, and the flat sides of the Morse taper post are aligned between the raised ridges. A washer having the desired aperture location is selected and a bolt is inserted through the aperture. The washer is then inserted into the boss cavity from the underside of the boss and the bolt shank is passed through the boss aperture, such that the bolt shaft extends upwardly from the boss inferior surface. The spherical engaging surface of the washer mates with and engages the similarly configured end wall of the cavity and the sides of the washer engage the sides of the boss cavity to inhibit rotation of the washer. The selected shape of the washer and location of the aperture determines the offset of the bolt. The threads of the bolt engage the threads of the Morse taper post and the bolt is rotated to urge the bolt and Morse taper post together.

FIGS. 17–28 illustrate a variety of other means by which various components can be assembled to one another to form an effective joint prosthesis system.

Figures 17, 18:
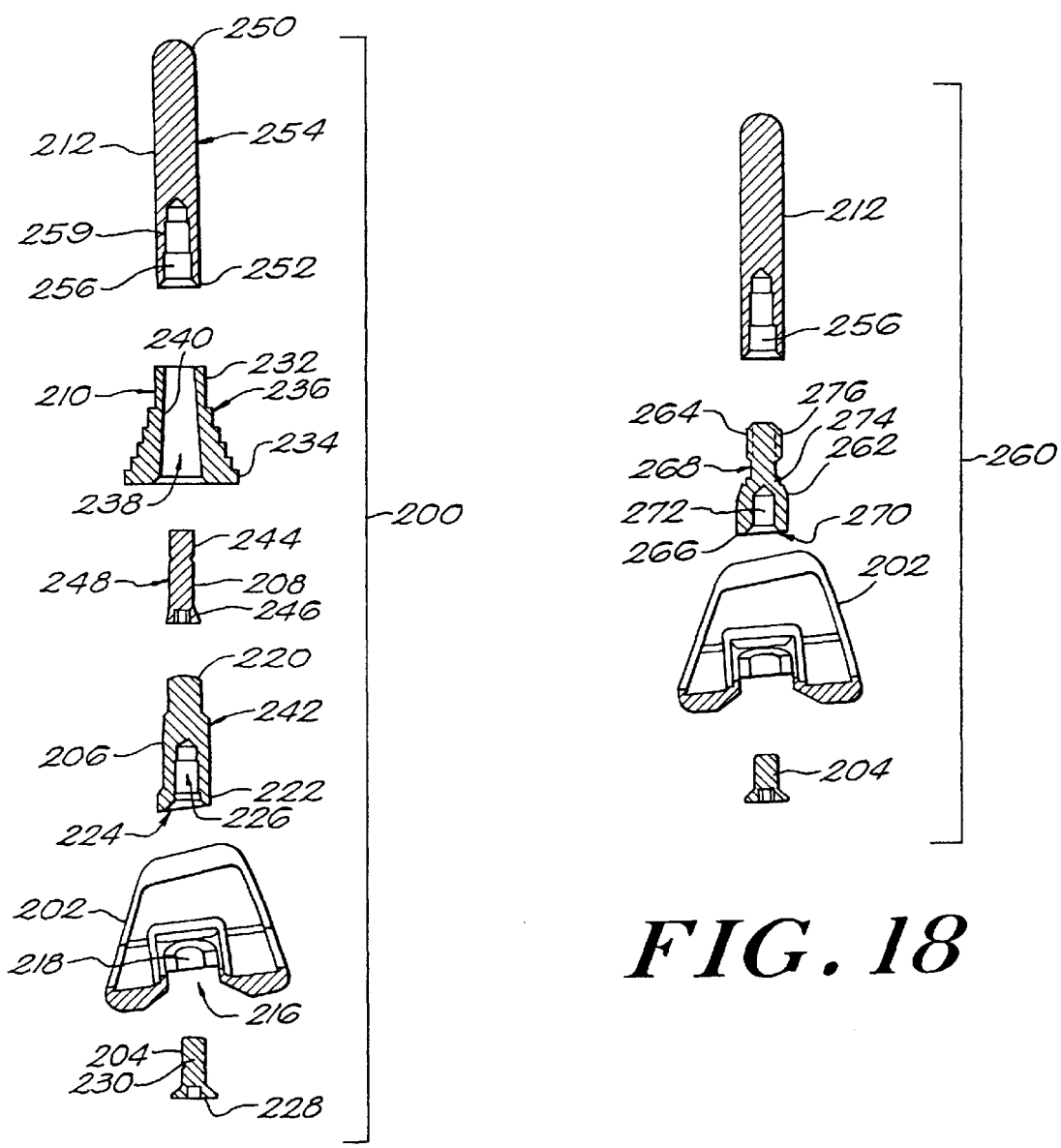
FIG. 17 is an exploded, sectional view of a joint prosthesis system according to the invention.
FIG. 18 is an exploded, sectional view of a joint prosthesis system according to another embodiment of the invention.

Referring to FIG. 17, prosthesis system 200 represents one embodiment of the invention. The system 200 includes a first prosthesis component 202, such as a femoral component of a knee prosthesis, a first bolt 204, an adapter element 206, a second bolt 208, a second prosthesis component 210, such as a metaphyseal augment, and a femoral stem 212.

The first prosthesis component or femoral component 202 has a first, superior surface (not shown) and second inferior surface 216 with an aperture 218 extending therebetween. The adapter element 206 has proximal 220 and distal 222 ends. The distal end has a mating surface 224 that abuts the first surface of the first prosthesis 202 when the prosthesis system is assembled. The distal end also includes a bore 226.

The adapter element 206 may be mated to the first prosthesis 202 by placing the mating surface 224 upon the first surface of the prosthesis component 202. The first bolt is then passed through the aperture 218 such that a head 228 of bolt 204 abuts the second surface 216 of the first prosthesis component 202 and a shaft 230 of the bolt extends through aperture 218 and into bore 226. The adapter element 206 and the first bolt 204 may be joined by mechanical interaction of threads (not shown) of the shaft 230 with complementary threads (not shown) within the bore 226, or by an interference fit of shaft 230 within bore 226.

The second prosthesis component 210, which may be a metaphyseal augment, has proximal 232 and distal 234 ends and an external, bone engaging surface 236, which may be irregularly shaped to accommodate a fit and/or bone ingrowth. A bore 238 extends between proximal and distal ends 232, 234. In one embodiment, illustrated in FIG. 17, the inner surface of 240 of bore 238 is tapered proximally. This tapering of the inner surface 240 of bore 238 is, as described below, effective to accommodate an interference fit between the second prosthesis component 210 and an adapter element 206. As shown in FIG. 17, the outer surface 242 of adapter 206 likewise is proximally tapered.

The system 200 also includes a second bolt 208 which has proximal and distal ends 244, 246 and an outer surface 248. The distal end 246 of the outer surface 248 may be smooth and may taper proximally over at least a portion thereof. The proximal end 244 of the outer surface 248 may include threads (not shown), or it may be proximally tapered as well.

Figures 21, 22:
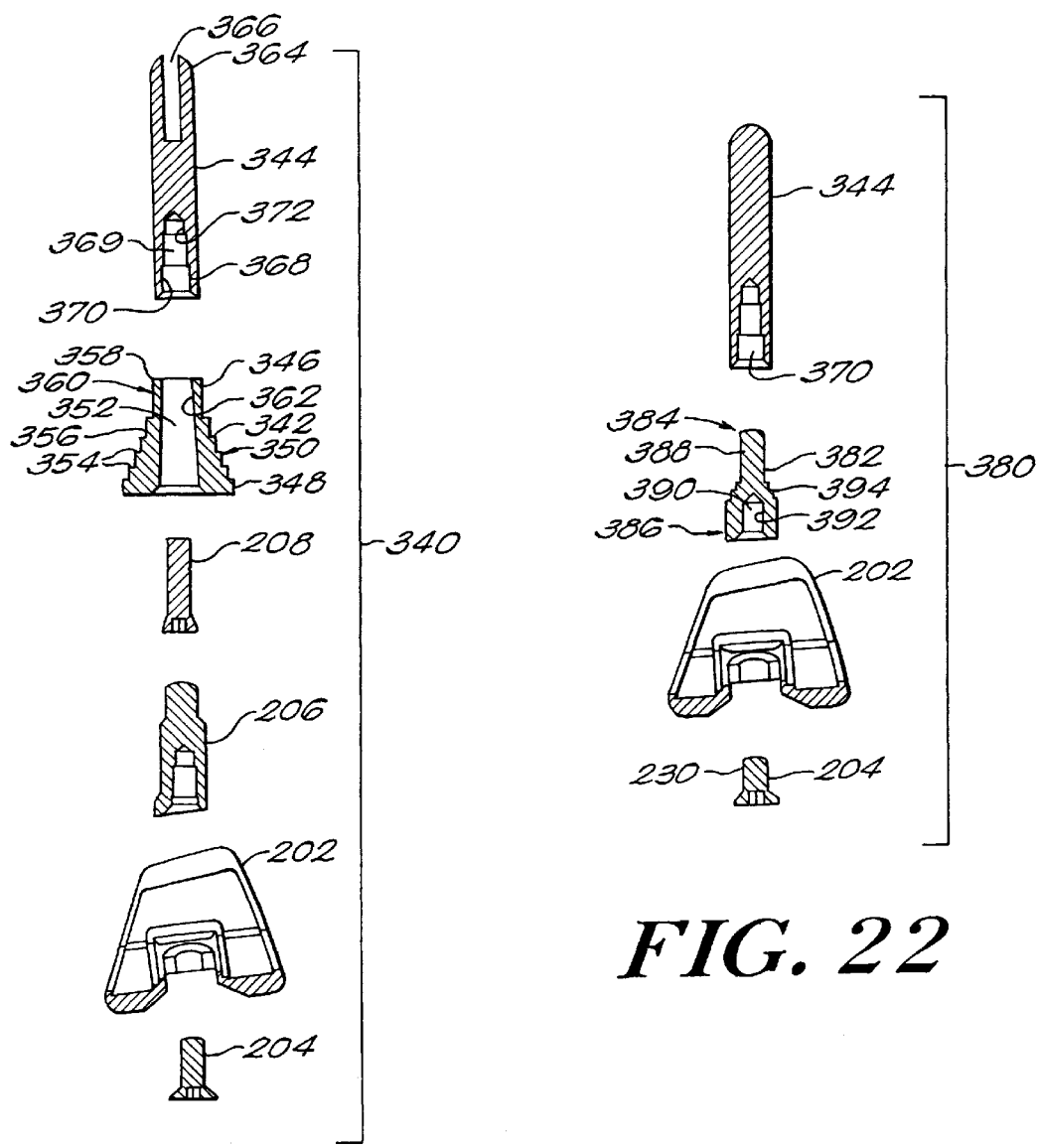
FIG. 21 is an exploded, sectional view of a joint prothesis system according to a further embodiment of the invention.
FIG. 22 is an exploded, sectional view of a joint prosthesis system according to another embodiment of the invention.

An additional element of the system 200 is a femoral stem 212 which is an elongate member having proximal and distal ends 250, 252 with an outer surface 254 extending therebetween. The distal end 252 of the femoral stem preferably includes a bore 256 that extends therein. As is known to those of ordinary skill in the art, the outer surface 254 of the femoral stem 212 may include external surface features (not shown), such as longitudinal grooves, to enhance fixation within the femur. Further, the proximal end 250 of the femoral stem may be slotted, as shown in FIG. 21.

The components of the prosthesis system 200 may be assembled as follows. The distal end 252 of the femoral stem 212 is positioned adjacent the proximal end 232 of the second prosthesis component 210, or augment. Thereafter, the second bolt 208 is inserted through the bore 238 of the augment 210 such that the distal end 246 of the outer surface interferingly engages the proximal end 232 of the inner surface 240 of bore 238, allowing the proximal end of the second bolt 208 to extend into the bore 256 of the femoral stem. The second bolt 208 is thus effective to mechanically join the femoral stem 212 to the second prosthesis component 210. This mechanical joinder may be by way of an engagement between external threads 244 on the proximal end of the second bolt 208 engaging complementary threads (not shown) within bore 256. Alternatively, the proximal end 244 of the second bolt 208 may be proximally tapered, instead of being threaded, and this surface may interferingly engage a complementarily tapered surface within bore 256 of femoral stem 212.

FIG. 18 illustrates a joint prosthesis system 260 that does not require a metaphyseal augment as a second prosthesis component. The system 260 includes a first prosthesis component 202, such as a femoral component of a knee prosthesis, a first bolt 204, an adapter element 262, and a femoral stem 212, which serves as a second prosthesis component. The first prosthesis component 202 and the first bolt component 204 and the femoral stem 212 are similar, if not identical, to the same elements described above with respect to FIG. 17.

The adapter 262 useful in system 260 includes a proximal end 264, a distal end 266, and an outer surface 268 that extends therebetween. The distal end 266 of adapter 262 includes a mating surface 270 and a bore 272 extends into the adapter element from the distal end 266 thereof. The outer surface 268 of the adapter element 262 is irregularly shaped. As illustrated, the distal end of the outer surface has a diameter greater than the proximal end of the outer surface. Thus, at an intermediate portion 274 the diameter of the outer surface of the adapter element narrows substantially such that the proximal end 264 appears as a member that extends from the distal end of the adapter element.

In the illustrated embodiment the proximal end 264 includes external threads 276 which mate with complementary threads (not shown) within bore 256 of femoral stem 212. In an alternative embodiment, proximal end 264 of adapter element of 262 is non-threaded, but instead it is proximally tapered. In this alternative embodiment the bore 256 of stem 212 is non-threaded and is proximally tapered in a manner complementary to that of the proximal portion 264 of adapter element 262, allowing for an interference fit of the femoral stem upon the adapter element.

The system 260 of FIG. 18 may be assembled by mounting the mating surface 270 of the adapter element upon the second surface 216 of the first prosthesis component 202. The adapter is secured to the femoral component by the first bolt, in a manner described above. Thereafter, the adapter element is joined to the femoral stem in an appropriate manner, either by threaded engagement or by interference fit.

Figures 19, 20:
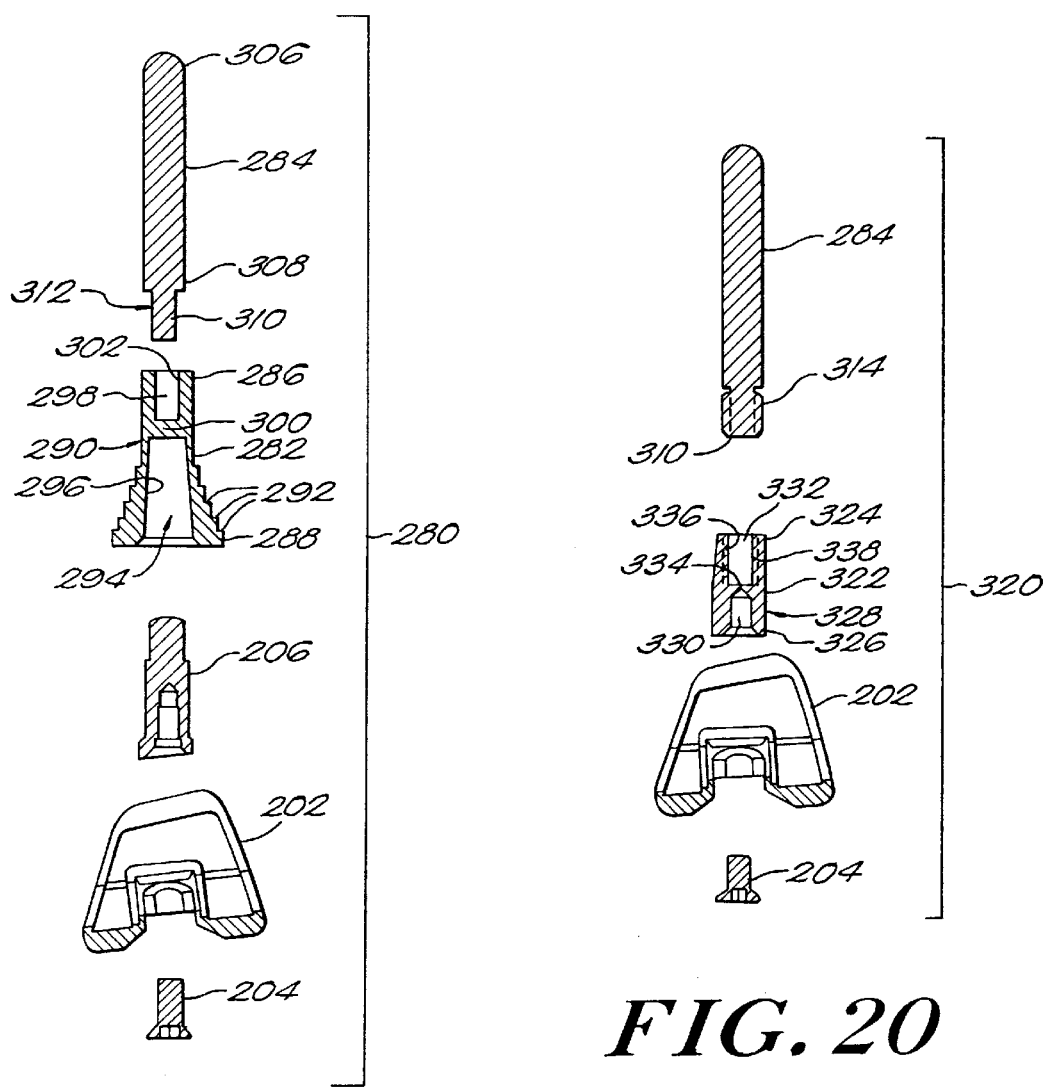
FIG. 19 is an exploded, sectional view of a joint prosthesis system according to a further embodiment of the invention.
FIG. 20 is an exploded, sectional view of a joint prosthesis system according to yet another embodiment of the invention.

FIG. 19 illustrates system 280 which is a variation of system 200 described in FIG. 17. System 280 includes the various components present in FIG. 17, including first prosthesis component 202, such as a femoral component of knee prosthesis, a first bolt 204, and an adapter element 206. System 280 also includes a metaphyseal augment 282 and a femoral stem 284, both of which differ from similar components described above with respect to FIGS. 17 and 18.

The metaphyseal augment 282, which serves as a second prosthesis component, includes proximal and distal ends 286, 288 with an outer surface 290 extending therebetween. The distal portion 288 of the outer surface 290 may be irregularly shaped, so as to include, for example, steps 292. The proximal portion 286 of the outer surface 290 may have a diameter substantially smaller than the diameter as measured at the distal end of the metaphyseal augment 282. Generally, the diameter of the proximal end 286 is substantially the same as the outer diameter of the femoral stem 284. The metaphyseal augment 282 also includes a distal blind bore 294 having an inner surface 296 which is proximally tapered. The distal bore 294 may extend over approximately 25 to 75 percent of the entire length of the metaphyseal augment 282, representing a distance of about 10 mm to 50 mm. The distal bore 294 tapers from a widest diameter at a distal end of the bore to a narrowest diameter at a proximal end of the bore of about 15 mm to 13 mm, respectively.

The metaphyseal augment 282 also includes a proximal bore 298 which extends into the augment from the proximal end 286 of the augment. A separating wall 300 can be utilized to separate the proximal and distal bores for each other. The proximal bore 298 may, in one embodiment, be non-tapered and include an inner surface 302 having threads (not shown). Although distal and proximal bores 294, 298 are shown as blind bores, one of ordinary skill in the art will appreciate that a single throughbore may alternatively be used.

The femoral stem 284 useful with system 280 has proximal and distal ends 306, 308. An elongate member 310 extends from the distal end 308 of stem 284. Preferably, the outer surface 312 of elongate member 310 includes threads (not shown) that are complementary to and matable with the threads within proximal bore 298.

The structure of system 280 is advantageous in that it eliminates the need for a second bolt since the femoral stem may be joined to the metaphyseal augment by threaded engagement of these two elements. Further, the metaphyseal augment and the adapter element are joined to one another by an interference fit.

The joint prosthesis system 320, illustrated in FIG. 20, is similar to that shown in FIG. 19 except that a metaphyseal augment is not included. System 320 includes a first prosthesis component 202 such as a femoral component of a knee prosthesis, a first bolt 204, and a femoral stem 284, all of which have structural features similar to those elements described above. System 320 utilizes an adapter element 322 that is slightly different than that described above with respect to FIGS. 17–19.

Adapter element 322 includes a proximal and distal ends 324, 326, with an outer surface 328 extending therebetween. A distal bore 330 is formed in the distal end of the adapter 322 while a proximal bore 332 is formed in the proximal end of adapter element 322. A separating wall 334 can separate bores 330 and 332 from each other. Alternatively, a single throughbore (not shown) can replace distal and proximal bores 330, 322.

Distal bore 330 may include internal threads (not shown) complementary to threads (not shown) on the shaft 230 of the first bolt 204. Alternatively, as noted above, both the shaft of the first bolt and the distal bore 330 may be proximally tapered to accommodate an interference fit.

The proximal bore 332 has an inner surface 336 that includes threads 338. Threads 338 are complementary to the threads 314 formed on the elongate member 310 of femoral stem 284.

FIG. 21 illustrates an alternative joint prosthesis system 340 that is similar to systems described above in that it includes a first prosthesis component 202, a first bolt 204, an adapter element 206 and a second bolt 208, all of which are structurally similar to those components described above. System 340 includes a metaphyseal augment 342, which serves as a second prosthesis component, and a femoral stem 344, both of which differ somewhat from similar components described above.

The metaphyseal augment 342 has proximal and distal ends 346, 348 with an outer surface 350 extending therebetween. Further, an internal bore 352 extends between the proximal and distal ends 346, 348 of the metaphyseal augment 342. The outer surface 350 of the metaphyseal augment may be irregularly shaped so as to include surface features such as steps 354 formed at least on a distal portion of the outer surface of the augment. As such, the steps 354 are on the outer surface 350 cause the augment to have an outer diameter that decreases sequentially from the distal end 348 to an intermediate portion 356. Proximal of the intermediate portion, the diameter of the metaphyseal augment 342 remains constant and it is substantially the same as the diameter of femoral stem 344.

The proximal portion 346 of the metaphyseal augment 342 includes a proximal extension 358. The proximal extension 358 includes an outer surface 360 which is substantially smooth and which tapers proximally. Preferably, the taper of the proximal extension has a length of about 2 mm to 9 mm.

The internal bore 352 that extends within metaphyseal augment 342 preferably is proximally tapered over at least a portion of its length. That is, the bore 352 tapers from distal end 348 to neck region 362. Thereafter, the bore has a substantially constant diameter, which may be slightly less than the diameter of the bore at the neck region thereof.

The femoral stem 344 may be similar in many respects to those described above in connection with other embodiments of the invention. Femoral stem 344 includes a proximal end 364 that has a longitudinal slot 366 formed therein. One of ordinary skill in the art will readily appreciate that such a slot may be desirable for some applications, but need not always be present in a femoral stem. Further, although only one slot is shown, multiple slots may be formed in the proximal end of the femoral stems.

The femoral stem 344 also includes a distal end 368 that has a blind bore 369 extending therein. The blind bore 368 can be characterized as having two sections: a distal, tapered section 370 and a proximal threaded section 372.

The distal section 370 has an inner surface that is tapered proximally over a length of about 3 mm to 10 mm. This proximally tapered inner surface is complementary to the taper of the proximal extension 358 of the metaphyseal augment 342 to enable an interference fit between a portion of the metaphyseal augment, i.e., the proximal extension 358 and the femoral stem.

The proximal section 372 of the bore 370 has a substantially constant diameter with an inner surface that includes threads (not shown). Preferably, the threads are complementary to the external threads formed on the proximal end of the second bolt 208.

Accordingly, the system 340 of FIG. 21 enables the metaphyseal augment to be joined to the first prosthesis component 202 and the adapter elements 206 and a press-fit manner. The femoral stem 344 is, in turn, joined to the metaphyseal augment by a combination of an interference fit of the proximal extension of the metaphyseal augment within a portion of the bore 370 of the femoral stem and by the threaded engagement of the second bolt 208 with portion 372 of the bore 370 of the femoral stem.

FIG. 22 illustrates joint prosthesis system 380, which is somewhat similar to system 340 shown in FIG. 21. As illustrated, system 380 includes a first prosthesis component 202, a first bolt 204 and a femoral stem 344, all of which are similar to prosthesis components described above. System 380 also includes an adapter element 382 which has proximal and distal ends 384, 386 with an outer surface 388 extending therebetween. The distal end 386 of adapter 382 includes a blind bore 390 having a threaded inner surface 392. Threaded inner surface 392 is constructed to be matable with the threaded shaft 230 of first bolt 204.

An intermediate portion 394 of the outer surface of the adapter element 382 is disposed between the proximal and distal portions 384, 386. The intermediate portion 394 extends over a distance of about 1 mm to 10 mm and is proximally tapered. Proximal portion 384 is disposed proximally of intermediate portion 394 and extends over a distance of about 2 mm to 9 mm. In the illustrated embodiment, the diameter of the proximal portion is substantially constant across its entire length. The proximal portion may also includes threads (not shown) which are matable with complementary threads on the inner surface 376 of femoral stem 344.

System 380 may be assembled by installing the femoral stem within a patient's femur and subsequently attaching the adapter element 382 to the femoral stem. The adapter element mates with the femoral stem through a combination of mechanical engagement between the threads and the proximal portion and the threads in the femoral stem as well as an interference fit between the tapered surface of intermediate portion 394 and the tapered distal section of the bore 370 of the femoral stem. Thereafter, the femoral component can be installed upon the femur and attached to the adapter element and the femoral stem through the first bolt 204. Alternatively, the prosthesis components can be preassembled and then implanted into the prepared femoral intramedullary canal.

Figures 23, 24:
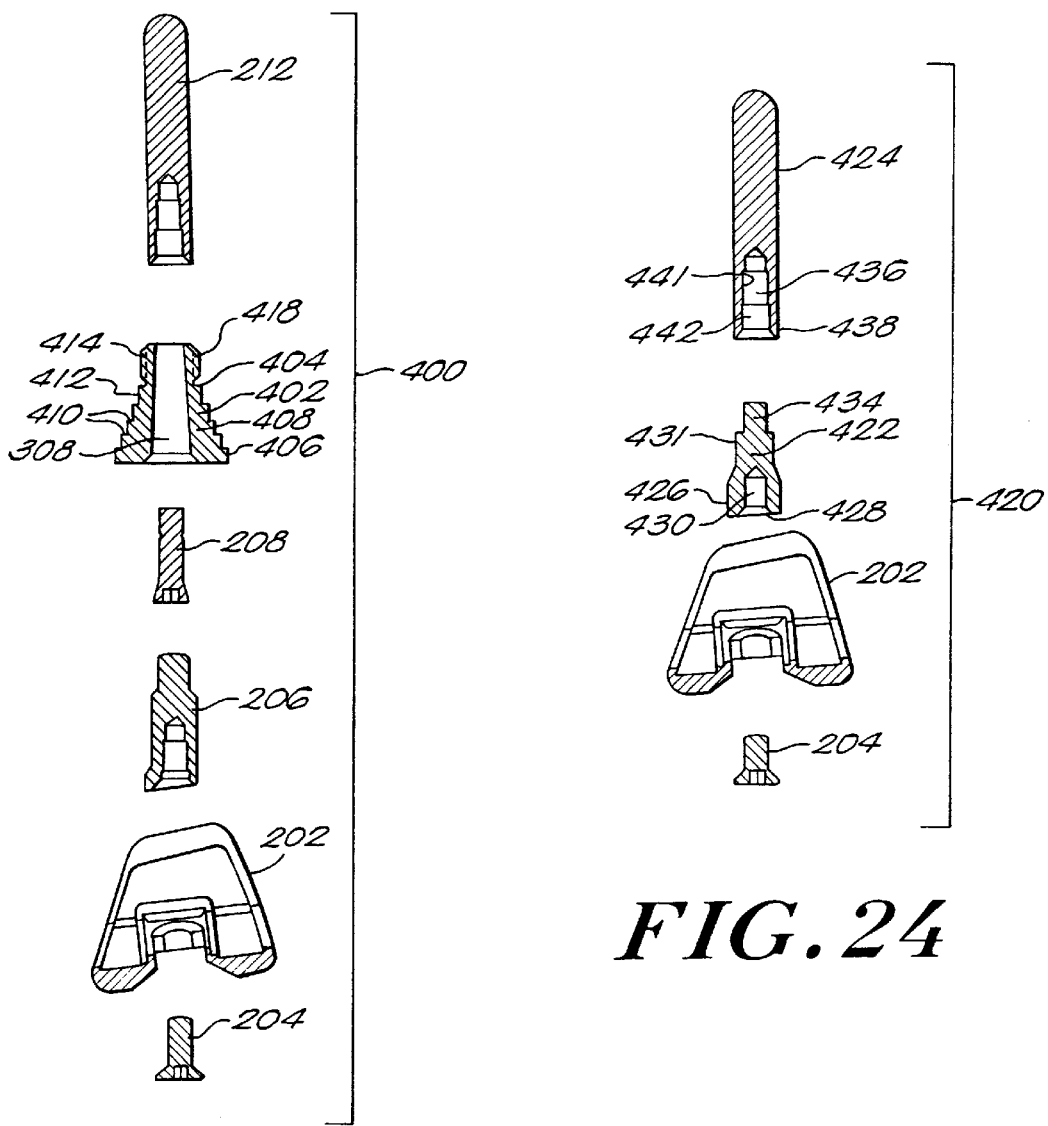
FIG. 23 is an exploded, sectional view of a joint prosthesis system according to a further embodiment of the invention.
FIG. 24 is an exploded, sectional view of a joint prosthesis system according to yet another embodiment of the invention.

FIG. 23 illustrates system 400 which includes a first prosthesis component 202, a first bolt 204, a second bolt 208, an adapter element 206, and a femoral stem 212, all of which are similar to components described above. In addition, system 400 includes a metaphyseal augment 402 which serves as a second prosthesis component.

The metaphyseal augment includes proximal and distal portions 404, 406 with an outer surface 408 extending therebetween. A distal portion of the outer surface may include surface features, such as steps 410, which cause the diameter of the distal portion of the metaphyseal augment 402 to decrease sequentially and proximally over a portion of the distal end. These proximal portion 404 of the metaphyseal augment 402 has a first segment 412 and a proximal extension 414. The first segment 412 is disposed adjacent to the distal portion 406 and includes a diameter that is substantially constant and which is substantially the same as the diameter of the femoral stem 212. The first segment 412 may extend over a distance of about 5 mm to 10 mm. The proximal extension 414 extends proximally from the first segment over a distance of about 2 mm to 9 mm. The proximal extension has an outer surface that includes threads 418. The diameter of the proximal extension is substantially constant along its entire length and is sufficient to enable the proximal extension to mate within the bore of the femoral stem. Preferably, the threads 418 are complementary with internal threads within the femoral stem.

The metaphyseal augment 402 includes a bore 348 having structural characteristics and dimensions similar to that described above with respect to FIG. 21.

One of ordinary skill in the art will readily appreciate that the system 400 can be implanted as follows. The femoral stem is inserted within a prepared cavity within a patient's femur. Thereafter, the preassembled prosthesis is implanted within the prepared femur.

FIG. 24 illustrates prosthesis system 420 which includes a first prosthesis component 202 and a first bolt 204, both of which are substantially identical to similar components described above. System 420 also includes an adapter element 422 and a femoral stem 424. The adapter element has a distal portion 426 with a substantially constant diameter that represents the greatest diameter of the adapter element 422. The distal portion 426 also includes a mating surface 428 within which is disposed a longitudinally oriented blind bore 430. The adapter element also includes an intermediate section 431 having a proximally non-tapered outer surface that extends over a distance of about 2 mm to 9 mm. A proximal extension 434, which is proximally threaded over a distance of about 5 mm to 10 mm extends from intermediate section 431.

The femoral stem 424 may have dimensions and structural features similar to those described above and which will be readily appreciated by one of ordinary skill in the art. A femoral stem 424 also includes a longitudinally oriented blind bore 436 that is formed in the distal end 438 thereof. The blind bore 436 includes a proximal section 441 extending over a length of about 5 mm to 10 mm which is proximally threaded so as to be complementary to the threads of the proximal extension 434. Disposed distally of this section of the bore is a distal bore section 442 which extends over a distance of about 3 mm to 10 mm and which is dimensioned proximally so as to provide an interference fit with the intermediate section 432 of the adapter element.

One of ordinary skill in the art will readily appreciate that system 420 can be preassembled or it can be assembled during surgery by first installing the femoral stem within a prepared cavity of a patient's femur. Thereafter, the adapter element is positioned within the blind bore 436 of the femoral stem 424 to achieve an interference fit. The first prosthesis component 202 can then be installed upon the mating surface 428 of the adapter element and secured thereto by first bolt 204.

Figure 25:
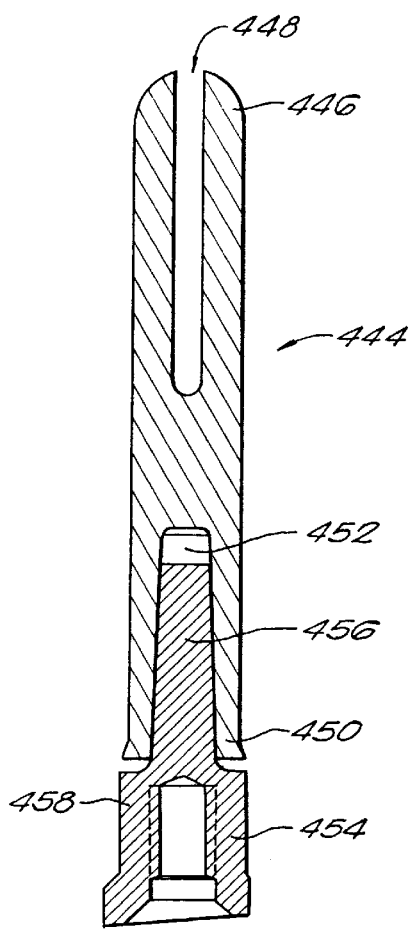
FIG. 25 is a sectional view of a portion of a partially assembled joint prosthesis system according to one embodiment of the present invention.
Figure 26:
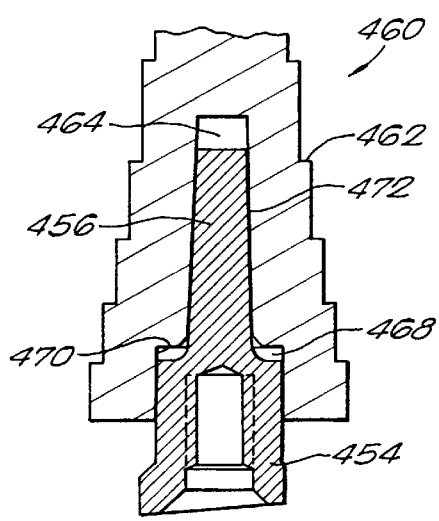
FIG. 26 is a sectional view of a portion of an assembled joint prosthesis system according to an embodiment of the present invention.

FIGS. 25 and 26 illustrate additional variations for joining various components of prosthesis systems.

In FIG. 25 a slotted femoral stem 444 includes a proximal end 446 having a longitudinal slot 448 disposed therein. This slot preferably extends over a distance of about 20 mm to 60 mm. A distal end 450 of the femoral stem includes a blind bore 452 which is tapered proximally over a length of about 5 mm to 15 mm. Femoral stem 444 is mateable with an adapter element 454 which includes an elongate proximal extension 456 that extends from a main body 458 of the adapter element. The proximal extension extends over a distance of about 4 mm to 14 mm and the outer surface thereof is proximally tapered so as to be complementary to the taper of the blind bore 452. The adapter element can be mateable to the first prosthesis component as described above.

FIG. 26 illustrates the metaphyseal augment 460 which includes a stepped outer surface 462. The proximal end (not shown) of the metaphyseal augment 460 can vary as noted above with respect to the various embodiments described herein. The metaphyseal augment includes a blind bore 464 formed in the distal end 466 thereof. Blind bore 464 includes a first, proximal section 468 which has an inner surface 470 that is proximally tapered over a distance of about 3 mm to 10 mm. The first, proximal section 468 communicates with a second, distal section 472 of the blind bore 464. The second, distal section 472 has an inner surface with a diameter that is substantially constant and which is greater than the widest diameter of the first, proximal section 468. The diameter of the distal section 472 may be in the range of about 5 mm to 15 mm and the distal section 472 may extend over a length of about 5 mm to 20 mm.

Figure 27:
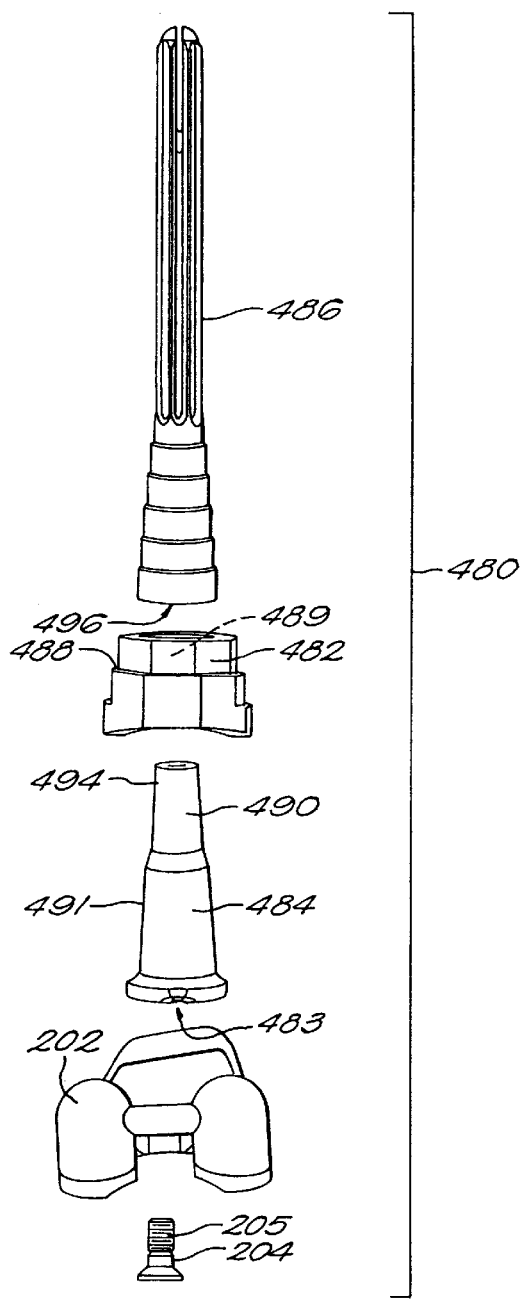
FIG. 27 is an exploded sectional view of a joint prosthesis system according to another embodiment of the invention.

FIG. 27 illustrates system 480. System 480 includes a first prosthesis component 202 and a first bolt 204, both of which are similar to items described above. System 480 also includes a metaphyseal augment 482, an adapter element 484 and a femoral stem 486.

The metaphyseal augment 482 may have a stepped outer surface 488 as described above. Metaphyseal augment 482 also includes a bore 489 which extends therethrough and which is tapered proximally over its entire length.

The adapter element 484 has an outer surface 491 that includes proximal and distal portions 490 and 492. The distal portion extends over a length of about 5 mm to 30 mm and is proximally tapered in a manner so as to be complementary to the taper of the bore 489 of the metaphyseal augment 482. The proximal portion of the adapter element is an elongate member 494 that extends from the distal portion 492 thereof. The proximal portion 490 extends over a length of about 5 mm to 20 mm and has an outer surface 494 that tapers proximally. A blind bore 493 is formed in the distal end of the adapter element. The blind bore may have a threaded inner surface that is mateable with threads 205 on the shaft of first bolt 204.

The system 480 also includes a femoral stem 486 which has a blind bore 496 formed in a distal end thereof. The blinded bore preferably has a tapered, inner surface that extends over a length of about 6 mm to 21 mm. The taper of the inner surface is complementary to that of the proximal extension of the adapter element to enable the adapter element and the femoral stem to interferingly engage each other in a frictional fit. Similarly, the metaphyseal augment and the distal portion of the adapter element frictionally engage each other by the interaction of the outer surface of the distal portion of the adapter element with the bore of the metaphyseal augment.

With respect to FIGS. 17–29, one of ordinary skill in the art will readily appreciate that the dimensions and sizes will vary depending upon the requirements of a given application. Tapered surfaces can, however, extend over a distance in the range of about 5 to 50 mm, and taper angles can range from about 1° to 15°.

Further, as noted above with respect to FIGS. 1–16, the systems illustrated in FIGS. 17–27 may be utilized in a manner in which the head 228 of the first bolt 204 is offset from the longitudinal axis of the shaft 230. This offset may range from about 0 to 5 mm.

Similarly, the mating surface of the various adapter elements used with the systems of FIGS. 17–29 may be parallel to the transverse axis of the adapter, or the mating surface may be angled with respect to the transverse axis. In a canted embodiment the mating surface is oriented at an angle of about 0° to 15°, and preferably about 2° to 10°, relative to the transverse axis of the mating surface. The angle can be oriented in the medial-lateral direction or in the anterior-posterior direction.

Figure 28A:
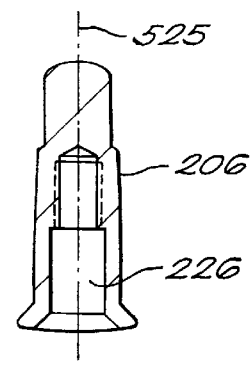
FIGS. 28A–28B are elevated views of various alternative adapter elements useful with the joint prosthesis system of the invention.
Figure 28B:
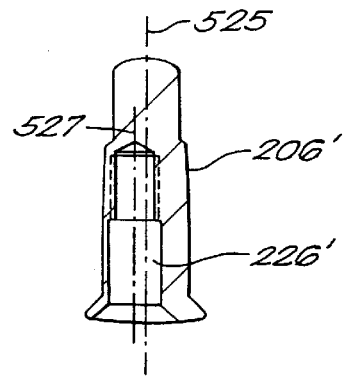

FIGS. 28A and 28B illustrate various alternative adapter elements useful with the present invention. As noted above with respect to FIGS. 1–16, the head 228 of the first bolt 204 may be offset from the longitudinal axis of the shaft 230. Such a system is useful with the adapter 206 shown in FIG. 28A in which a bore 226 is co-linear with the longitudinal axis 525 of the adapter element 206.

FIG. 28B illustrates an adapter element that obviate the need for an offset bolt. As shown in FIG. 28B bore, 226' is disposed within adapter element 206' such that the longitudinal axis 527 of bore 206' is offset, e.g., by about 1 to 5 mm, for longitudinal axis 525 of adapter 206'. A variety of additional options may be provided, as noted above, by altering the angle of the mating surface and the degree of offset.

Further, the bore 226' need not extend into the adapter element 206' in an orientation parallel to the longitudinal axis 525. Instead, bore 226' may be oriented at an angle relative to longitudinal axis 525. The angle (not shown) may be equivalent to the angle at which the mating surface is oriented. Such a design can be useful to reduce torsional stresses on the bolt and to allow additional clearance to increase the bolt shoulder and head size.

Figure 29:
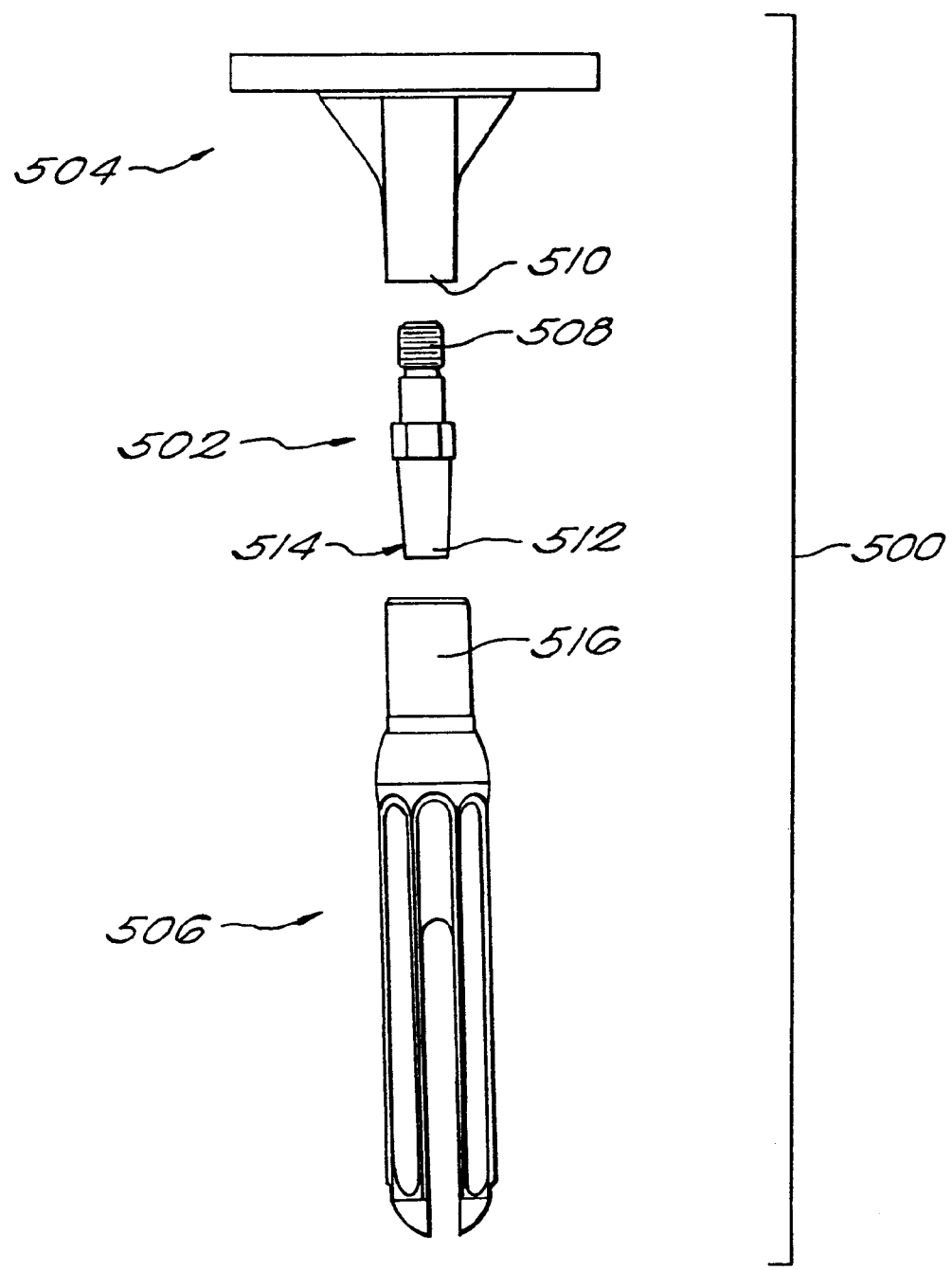
FIG. 29 is an exploded, front view of a joint prosthesis system according to another embodiment of the invention in which a tibial prosthesis component is illustrated.

FIG. 29 illustrates a prosthesis system 500 in which an adapter element 502 assists in connecting a first prosthesis component, such as tibial tray 504, to a second prosthesis component, such as a tibial stem 506. The adapter element 502 has a threaded proximal end 508 which is matable with a complementary threaded bore formed in the distal end 510 of tibial tray 504. The distal end 512 of the adapter element 502 includes an outer surface 514 which tapers distally. Tapered outer surface 514 mates with a bore (not shown) having a complementary tapered surface that is formed in the proximal end 516 of stem 506.

The system is assembled by press fitting the distal end 512 of the adapter 502 upon the proximal end 516 of stem 506. Thereafter, the adapter is joined to the tibial tray 504 by threading the proximal end 508 of adapter 502 within the bore in the distal end 510 of the tibial tray 504.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

What is claimed is:

1. A modular joint prosthesis system, comprising:
   a first prosthesis component having a first surface, a second surface, and an aperture extending therebetween;
   a modular adapter element with a length along a longitudinal axis thereof greater than a width along a transverse axis thereof, the modular adapter element having a first end mountable adjacent the first surface of the first prosthesis component and a second, mating end engagable with a second prosthesis component, the first end including a bore extending into the modular adapter element; and
   a first bolt including a head portion engagable with the second surface of the prosthesis component to inhibit movement of the bolt component through the aperture in the first prosthesis component, and an elongate shaft portion extending from the head portion of the bolt, the elongate shaft portion having a length sufficient to protrude through the aperture in the first prosthesis component and beyond the first surface of the prosthesis component into the bore in the first end of the modular adapter element to secure the modular adapter element to the first surface of the first prosthesis component.

2. The system of claim 1 wherein the first bolt and the modular adapter element are threadingly engagable with each other.

3. The system of claim 2 wherein the first bolt has external threads and the bore in the first end of the adapter element has internal threads.

4. The system of claim 1 wherein the bore in the first end of the adapter element is offset from the longitudinal axis of the adapter element.

5. The system of claim 4 wherein the bore in the first end of the adapter element is offset from the longitudinal axis of the adapter element in the anterior-posterior plane.

6. The system of claim 5 wherein the bore in the first end of the adapter element is offset by 0.5 to 5.0 mm in a direction that is anterior or posterior to the longitudinal axis of the adapter element.

7. The system of claim 1 wherein the first end of the adapter element has a mounting surface that is mountable on the first surface of the prosthesis component.

8. The system of claim 7 wherein the mounting surface is parallel to a transverse axis of the adapter element.

9. The system of claim 7 wherein the mounting surface is angled with respect to the transverse axis of the adapter element.

10. The system of claim 9 wherein the mounting surface is angled with respect to the transverse axis of the adapter element in the medial-lateral plane.

11. The system of claim 9 wherein the mounting surface forms an angle with the transverse axis of the adapter element in the medial-lateral plane in the range of about 2° to 10°.

12. The system of claim 1 wherein the mating end of the adapter element has a diameter that tapers proximally over at least a portion thereof.

13. The system of claim 12 wherein the mating end tapers over a distance of about 5 to 50 mm.

14. The system of claim 12 wherein the diameter of the mating end tapers at an angle in the range of approximately 1° to 15°.

15. The system of claim 1 wherein the mating end of the adapter element has a longitudinally oriented blind bore extending therein.

16. The system of claim 15 wherein the longitudinally oriented blind bore includes internal threads.

17. The system of claim 15 wherein the longitudinally oriented blind bore tapers distally from an opening in a proximal end thereof.

18. The system of claim 1 wherein the mating end of the adapter element has external threads formed over at least a portion of an outer surface thereof.

19. The system of claim 18 wherein the mating end of the adapter element has an outer surface with external threads formed on a proximal end thereof and wherein a portion of the mating end distally adjacent to the external threads has a diameter that increases distally of the external threads.

20. The system of claim 12, wherein the second prosthesis component is a metaphyseal augment having proximal and distal ends, the metaphyseal augment having a bore extending longitudinally therethrough wherein at least a portion of the bore tapers from the distal end of the augment to the proximal end of the augment and wherein the system further comprises:
   an elongate second bolt having proximal and distal ends wherein at least a portion of the proximal end of the second bolt includes external threads and at least a portion of the second bolt distal to the external threads has an outer surface with a taper complementary to the bore of the augment, the second bolt being matable within the bore of the augment such that at least the external threads of the second bolt protrude proximally from the augment; and
   an elongate femoral stem mountable upon the proximal end of the augment, the femoral stem having proximal and distal ends, the distal end including a blind bore with internal threads that are matable with the external threads of the second bolt.

21. The system of claim 20 wherein the proximal end of the femoral stem includes at least one longitudinal slot.

22. The system of claim 18, wherein the second prosthesis component is a femoral stem having proximal and distal ends with an internally threaded blind bore disposed in the distal end of the femoral stem, the femoral stem being matable with the adapter element by the engagement of the external threads of the adapter element with the internally threaded blind bore.

23. The system of claim 12 wherein the second prosthesis component is a femoral stem having proximal and distal ends with a proximally tapered blind bore disposed in the distal end of the femoral stem, the femoral stem being matable with the adapter element by the engagement of the mating end of the adapter element with the blind bore of the femoral stem.

24. The system of claim 12, wherein the second prosthesis component is a metaphyseal augment having proximal and distal ends, a tapered bore extending partially into the distal end of the augment, and an internally threaded bore extending partially into the proximal end of the augment, and wherein the system further comprises:
   an elongate femoral stem mountable upon the proximal end of the augment, the femoral stem having proximal and distal ends wherein the distal end includes an externally threaded extension member that is matable within the internally threaded bore at the proximal end of the augment.

25. The system of claim 24 wherein the proximal end of the femoral stem includes at least one longitudinal slot.

26. The system of claim 18, wherein the second prosthesis component is an elongate femoral stem mountable upon the proximal end of the adapter element, the femoral stem having proximal and distal ends wherein the distal end includes an externally threaded extension member that is matable within the longitudinally oriented blind bore formed in the mating end of the adapter element.

27. The system of claim 26 wherein the proximal end of the femoral stem includes at least one longitudinal slot.

28. The system of claim 12, wherein the second prosthesis component is a metaphyseal augment having proximal and distal ends, a bore extending longitudinally therethrough wherein at least a portion of the distal end of the augment tapers proximally, and an extension formed at the proximal end of the augment, the extension having an outer surface that tapers proximally, and wherein the system further comprises:
   an elongate second bolt having proximal and distal ends wherein at least a portion of the proximal end of the second bolt includes external threads and at least a portion of the second bolt distal to the external threads has a taper complementary to the bore of the augment, the second bolt being matable within the bore of the augment such that at least the external threads protrude proximally from the augment; and
   an elongate femoral stem mountable upon the proximal end of the augment, the femoral stem having proximal and distal ends wherein the distal end includes a blind bore defined by a distal portion with a tapered inner surface complementary to and matable with the outer surface of the extension on the augment, and a proximal portion with an internally threaded inner surface that is matable with the external threads of the bolt.

29. The system of claim 28 wherein the proximal end of the femoral stem includes at least one longitudinal slot.

30. The system of claim 18, wherein the second prosthesis component is a femoral stem having proximal and distal ends with a blind bore disposed in the distal end of the femoral stem, the bore having a proximal portion with internal threads and a distal portion with an inner diameter that tapers proximally from an opening of the blind bore to the internal threads, the femoral stem being matable with the adapter element by a combination of the engagement of the external threads of the adapter element with the internal threads of the blind bore and interference between the tapered inner diameter of the blind bore and the mating end of the adapter element.

31. The system of claim 30 wherein the proximal end of the femoral stem includes at least one longitudinal slot.

32. The system of claim 12, wherein the second prosthesis component is a metaphyseal augment having proximal and distal ends, a bore extending longitudinally therethrough wherein at least a portion of the bore tapers proximally from the distal end of the augment, and an extension formed at the proximal end of the augment, and wherein the system further comprises:
- an elongate second bolt having proximal and distal ends wherein at least a portion of the proximal end of the second bolt includes external threads and at least a portion of the second bolt has an outer surface with a taper complementary to the bore of the augment, the second bolt being matable within the bore of the augment such that at least the external threads of the second bolt protrude proximally from the augment; and
- an elongate femoral stem mountable upon the proximal end of the augment, the femoral stem having proximal and distal ends wherein the distal end includes a blind bore with an internally threaded proximal portion matable with the external threads of the second bolt, and a non-threaded distal portion having dimensions effective to receive the extension of the augment.

33. The system of claim 32, wherein the proximal end of the femoral stem includes at least one longitudinal slot.

34. The system of claim 12, wherein the second prosthesis component is an elongate femoral stem mountable upon the adapter element, the femoral stem having proximal and distal ends wherein the distal end includes a blind bore with an internal surface having a taper complementary to and interferingly engagable with the mating end of the adapter element.

35. The system of claim 34 wherein the proximal end of the femoral stem includes at least one longitudinal slot.

36. The system of claim 1 wherein the mating end of the adapter element includes an extension member extending proximally from a shoulder formed on an intermediate portion of the adapter element, the extension member having a proximally tapered outer surface.

37. The system of claim 36 wherein the second prosthesis component is an elongate femoral stem that is mountable upon the adapter element, the femoral stem having proximal and distal ends with a longitudinal blind bore formed in the distal end thereof, the longitudinal blind bore having an inner surface with a taper complementary to and matable with the proximally tapered outer surface of the extension member.

38. The system of claim 37 wherein the longitudinal blind bore formed in the femoral stem has a first, distal portion with a substantially constant diameter and a second, proximal portion with a proximally tapered diameter complementary to and matable with the extension member, the first, distal portion having a diameter greater than a widest diameter of the second, proximal portion.

39. The system of claim 37 wherein the proximal end of the femoral stem includes a longitudinal slot.

40. The system of claim 1 wherein the prosthesis component is a femoral component of a knee joint prosthesis.

41. The system of claim 1, wherein the second prosthesis component is a metaphyseal augment having proximal end distal ends, the metaphyseal augment including a bore extending out from the distal end at least partially into the augment, and an elongate extension member formed at the proximal end of the augment, and wherein the system further comprises:
- an elongate femoral stem mountable upon the proximal end of the augment, the femoral stem having proximal and distal ends, wherein the distal end includes a blind bore with which the extension member of the augment is matable.

42. The system of claim 41, wherein the proximal end of the adapter element includes external threads that matingly engage threads formed within the bore at the distal end of the augment.

43. The system of claim 41, wherein the proximal end of the adapter element is proximally tapered such that the adapter element is interferingly engageable with a corresponding taper within the bore at the distal end of the augment.

44. The system of claim 41, wherein the extension member of the augment includes external threads that are matingly engageable with threads formed within the blind bore of the femoral stem.

45. The system of claim 41, wherein the extension member of the augment is proximally tapered over at least a portion of the length thereof such that the augment is interferingly engageable with a corresponding taper within the blind bore of the femoral stem.

46. The system of claim 1, wherein the second prosthesis component is a metaphyseal augment having proximal and distal ends with a bore extending longitudinally therethrough wherein at least a portion of the bore tapers from the distal end of the augment to the proximal end of the augment and wherein the system further comprises:
- a proximally extending member formed on the second end of the adapter element, the member being proximally tapered;
- a proximally tapered outer surface of the adapter element that is complementary to the taper of the bore of the augment to enable the adapter element to be matable within the bore of the augment such that the proximally extending member protrudes therefrom; and
- an elongate femoral stem mountable upon the proximal end of the augment, the femoral stem having proximal and distal ends, wherein the distal end includes a proximally tapered blind bore that is matable with the proximally extending member of the adapter element.

47. A modular joint prosthesis system, comprising:
- a first prosthesis component having a first surface, a second surface, and an aperture extending therebetween;
- a modular adapter element having a first end mountable adjacent the first surface of the prosthesis component and a second, mating end engagable with a second prosthesis component, the first end including a blind bore extending into the modular adapter element; and
- a first fastening element including a head portion engagable with the second surface of the prosthesis component to inhibit movement of the fastening element through the aperture in the prosthesis component, and an elongate shaft portion extending from the head portion of the fastening element, the elongate shaft portion having a length sufficient to protrude through the aperture in the prosthesis component and into the bore in the first end of the modular adapter element to secure the modular adapter element to the first surface of the prosthesis component.

48. A modular knee joint prosthesis, comprising:
- a femoral component having an articulation surface and an opposed bone-engaging surface, the bone-engaging surface including a stabilizing component integral with the femoral component and raised above a nominal bone-engaging base surface wherein a superior portion of the stabilizing component is mountable within the femur and an inferior portion of the stabilizing component defines a cavity within which a tibial eminence is engaged, the stabilizing component having an aperture extending between the superior and inferior portions thereof;

a modular adapter element having a first end mountable adjacent the superior portion of the stabilizing component and a mating end engagable with a second prosthesis component, the first end including a bore extending into the modular adapter element; and a first bolt including a head portion engagable with the inferior portion of the stabilizing component to inhibit movement of the bolt component through the aperture in the stabilizing component, and an elongate shaft portion extending from the head portion of the bolt, the elongate shaft portion having a length sufficient to protrude through the aperture in the stabilizing component and into the bone in the first end of the modular adapter element to secure the modular adapter element to the superior portion of the stabilizing component.

49. A joint prosthesis system, comprising:

a first prosthesis component including a bore with an internally threaded surface;

an adapter element having a first end with an externally threaded surface that is matable with the internally threaded surface of the first prosthesis component, and a second end having a distally tapered surface; and a second prosthesis component having at a first end a bore with an internal, tapered surface that is matable with the distally tapered surface of the adapter element.

* * * * *